United States Patent
Ishii et al.

(10) Patent No.: US 7,649,094 B2
(45) Date of Patent: Jan. 19, 2010

(54) OPTICALLY ACTIVE COMPOUNDS, METHOD FOR KINETIC OPTICAL RESOLUTION OF CARBOXYLIC ACID DERIVATIVES AND CATALYSTS THEREFOR

(75) Inventors: Yutaka Ishii, Osaka (JP); Yasushi Miki, Osaka (JP); Yoshiro Furukawa, Osaka (JP); Satoshi Murakami, Osaka (JP)

(73) Assignee: Daiso Co., Ltd., Osaka (JP)

( * ) Notice: Subject to any disclaimer, the term of this patent is extended or adjusted under 35 U.S.C. 154(b) by 901 days.

(21) Appl. No.: 10/502,750

(22) PCT Filed: Jan. 31, 2003

(86) PCT No.: PCT/JP03/00965

§ 371 (c)(1),
(2), (4) Date: Mar. 11, 2005

(87) PCT Pub. No.: WO03/064420

PCT Pub. Date: Aug. 7, 2003

(65) Prior Publication Data

US 2005/0154209 A1    Jul. 14, 2005

(30) Foreign Application Priority Data

Jan. 31, 2002 (JP) ............................. 2002-022690
Sep. 24, 2002 (JP) ............................. 2002-276579

(51) Int. Cl.
C07D 453/04 (2006.01)
C07D 215/20 (2006.01)

(52) U.S. Cl. ..................................... 546/134; 546/177

(58) Field of Classification Search ................. 546/134, 546/177
See application file for complete search history.

(56) References Cited

FOREIGN PATENT DOCUMENTS

DE          623694      * 12/1935
WO      WO 02/10096 A1   2/2002
WO      WO 03/011799 A1  2/2003

OTHER PUBLICATIONS

Dijkstra et al. J. Am. Chem. Soc. 1989, 111(21), 8069-76; CAS Abstract and structure attached.*
Dijkstra et al. J. Am. Chem. Soc. 1989, 111(21), 8069-76.*
Suzuki et al. Bull. Chem. Soc. Jpn. 1988, 61, 1999-2005.*
Neff et al. Helvetica Chimica Acta 1991, 74(3), 508-16.*
Shah et al. (Journal of the Institution of Chemists 1987, 59(6), 249-50; see CAS abstract and structures herein).*
Communication—Supplementary European Search Report for EP 03 70 3112, Feb. 1, 2005.
Kun et al., "Heterogeneous asymmetric reactions Part 17. Asymmetric hydrogenation of 2-methy1-3-pentenoic acid over cinchona modified pd/A1203 catalysts" Applied Catalysis A, vol. 203, 2000, pp. 71-79, XP002313783.
International Search Report for PCT/JP03/00965 mailed on May 20, 2003.
J. Hang et al., "Asymmetric Synthesis of α-Amino Acids via Cinchona Alkaloid-Catalyzed Kinetic Resolution of Urethane-Protected of α-Amino Acid N-Carboxyanhydrides", Journal of the American Chemical Society, 2001, vol. 123, No. 50, pp. 12696-12697.
M. von Arx et al., "A New Reaction Pathway in the Enantioselective Hydrogenation of Activated Ketones on Cinchona-Modified Platinum", Journal of Catalysis, 2001, vol. 202, No. 1, pp. 169-176.
B. Torok et al., "Asymmetric Sonochemical Reactions Enantioselective Hydrogenation of α-Ketoesters Over Platinum Catalysts", Ultrasonics Sonochemistry, 2000, vol. 7, No. 4, pp. 151-155.
M. von Arx et al., "First Enantioselective Hydrogenation of a Trifluoro-β-Ketoester with Cinchona-Modified Platinum", Journal of Catalysis, 2000, vol. 193, No. 1, pp. 161-164.
H.U. Blaser et al., "Heterogeneous Enantioselective Hydrogenation of Ethyl Pyruvate Catalyzed by Cinchona-Modified Pt Catalysts: Effect of Modifier Structure", Journal of the American Chemical Society, 2000, vol. 122, No. 51, pp. 12675-12682.
A.J. Blake et al., "The Highly Enantioselective Transformation of Silylketenes Into α-Silylthioesters Catalysed by Cinchona Alkaloids", Tetrahedron Letters, 2001, vol. 42, No. 15, pp. 2877-2881.
K. Borszeky et al., "Enantioselective Hydrogenation of α, β-Unsaturated Carboxylic Acids Over Cinchonidine Modified Palladium: Nature of Modifier—Reactant Interaction", Journal of Catalysis, 1999, vol. 187, No. 1, pp. 160-166.

(Continued)

Primary Examiner—Rebecca L Anderson
Assistant Examiner—Jason Nolan
(74) Attorney, Agent, or Firm—Cheng Law Group, PLLC

(57) ABSTRACT

The present invention provides a method of kinetic optical resolution of carboxylic acid derivatives using specific optically active catalysts. A racemic or diastereomeric mixture of carboxylic acid derivatives of the formula (A) is reacted with a nucleophile in the presence of an optically active catalyst to form an optically active nucleophile derivative of the formula (B). The catalyst is an optically active compound represented by the formula (C) or (D) [wherein $R^1$ is a substituted or unsubstituted, saturated or unsaturated, straight-chain, branched or alicyclic aliphatic hydrocarbon group which can have a heteroatom, $R^2$ is ethyl or vinyl, and $R^5$ is hydrogen or methoxy respectively].

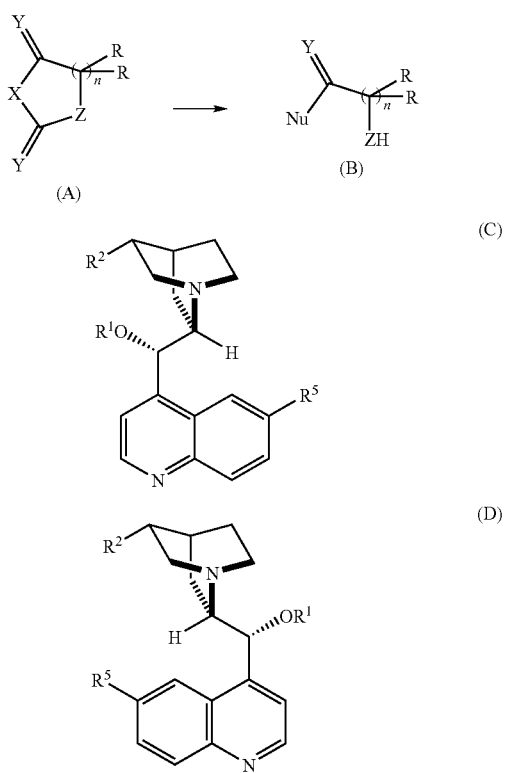

OTHER PUBLICATIONS

D. Ferri et al., "Enhanced Enantioselectivity in Ethyl Pyruvate Hydrogenation Due to Competing Enantioselective Aldol Reaction Catalyzed by Cinchonidine", Journal of Catalysis, 2000, vol. 193, No. 1, pp. 139-144.

L. Tang et al., "Dynamic Kinetic Resolution via Dual-Function Catalysis of Modified Cinchona Alkaloids: Asymmetric Synthesis of α-Hydroxy Carboxylic Acids", Journal of the American Chemical Society, 2000, vol. 124, No. 12, pp. 2870-2871.

J. Hang et al., "Development of a Rapid Room-Temperature Dynamic Kinetic Resolution for Efficient Asymmetric Synthesis of α-Aryl Amino Acids", Organic Letters, 2002, vol. 4, No. 19, pp. 3321-3324.

\* cited by examiner

3 Claims, No Drawings

OPTICALLY ACTIVE COMPOUNDS, METHOD FOR KINETIC OPTICAL RESOLUTION OF CARBOXYLIC ACID DERIVATIVES AND CATALYSTS THEREFOR

TECHNICAL FIELD

The present invention relates to a method of kinetic optical resolution of carboxylic acid derivatives derived from carboxylic acids such as amino acids, more particularly to a method of kinetic optical resolution wherein carboxylic acid derivatives derived from racemic or diastereomeric mixtures of chiral carboxylic acid compounds are reacted with nucleophiles in the presence of optically active catalysts to obtain optically active substances. The present invention also relates to the catalysts to be used for the above-mentioned method of optical resolution and further to novel optically active compounds which are useful as, for example, the above-mentioned catalysts.

BACKGROUND ART

The demand for optically active compounds has grown rapidly in recent years, and particularly demand for pharmaceutical intermediates in the pharmaceutical industry is increasing. Accordingly, a method of obtaining optically active compounds efficiently is intensively studied. One method of obtaining optically active compounds is an optical resolution method. Preferential crystallization, diastereomer resolution, kinetic resolution and the like are known as the optical resolution methods. Since the preferential crystallization has a narrow scope of application, obtainable compounds are remarkably limited. The diastereomer resolution requires a stoichiometric resolving agent and multi stages, and its operation is troublesome. On the other hand, the kinetic resolution method is a technique for performing optical resolution characterized by utilizing differences in reaction rate between racemates and enantiomers caused by performing reactions using optically active catalysts, thereby reacting only a specific enantiomer preferentially. The kinetic resolution using enzymes mainly comes in practice and is an effective method for obtaining optically active amino acids, alcohols and the like. However, since the kinetic resolution with enzymes generally requires long time for the reactions, and concentrations of substrates must be diluted in order to obtain high optical yields, this method is unsuitable for obtaining large amounts of optically active compounds.

Some studies of kinetic optical resolution by chemical techniques have been reported. For example, as a chemical method of optically resolving carboxylic acid derivatives such as amino acids, an optical resolution by alcoholysis of urethane-protected amino acid-N-carboxy anhydrides (UNCA) using cinchona alkaloid derivatives as catalysts was reported recently (Deng, L. et al. J. Am. Chem. Soc., 2001, 123, 12696-12697). This report states that quinidine, which is cinchona alkaloid, is effective as a catalyst in these reactions, and use of $(DHQD)_2AQN$ and DHQD-PHN, which are quinidine derivatives having alcohol moiety protected with an aryl group, leads to more efficient optical resolution. However, since $(DHQD)_2AQN$ and DHQD-PHN are difficult to synthesize, very expensive and hardly available, they are unsuitable for optical resolution in large amounts. It is necessary to use quinidine, which is readily available and inexpensive, in order to perform optical resolution in large amounts, but use of quinidine causes issues in recycling of the catalyst, namely, quinidine itself is reacted with UNCA to give by-products, which lowers purity of the recovered catalyst. Using $(DHQD)_2AQN$ and quinidine as catalysts, optical resolution in high substrate concentrations causes the problem that enantiomer selectivity is lowered. Accordingly, development of new catalysts which are readily available and stable and have high optical resolution ability is desired.

DISCLOSURE OF THE INVENTION

Studying precisely kinetic resolution by a chemical technique in view of the above-mentioned points, the present inventors found that kinetic optical resolution of carboxylic acid derivatives can be performed efficiently by using specific optically active catalysts, and complete the present invention.

The present invention relates to a method of a kinetic optical resolution of a carboxylic acid derivative, wherein a racemic or diastereomeric mixture of chiral carboxylic acid derivatives represented by the following general formula (A),

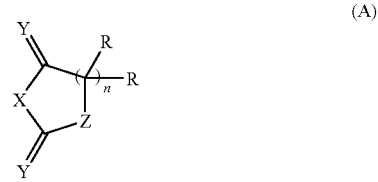

(A)

[wherein X is NR', an oxygen atom or a sulfur atom, Y is an oxygen atom or a sulfur atom, Z is NR', an oxygen atom or a sulfur atom, plural Rs, the same or different, are substituted or unsubstituted, saturated or unsaturated, straight-chain, branched or alicyclic aliphatic hydrocarbon groups which can have a heteroatom, substituted or unsubstituted aromatic hydrocarbon groups, substituted or unsubstituted heterocyclic groups, or noncarbon substituents or atoms, and n is an integer of 1 or 2, when n is 1, two Rs are not the same, and when n is 2, two Rs are not the same at at least one of adjacent two carbon atoms to which Rs are linked, and R' in X and Z has the same meaning as that of the above-mentioned R or is acyl, sulfonyl, oxycarbonyl or aminocarbonyl.], is reacted with a nucleophile (Nu-H) in a solvent in the presence of an optically active catalyst, thereby obtaining a nucleophile derivative which is rich in one enantiomer or diastereomer represented by the following general formula (B),

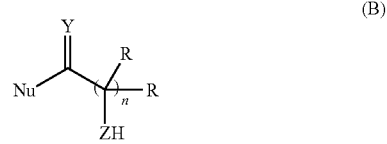

(B)

[wherein Nu is OR, $NR_2$ or SR, and Y, Z, R, n and R in Nu have the same meanings as those mentioned above.]

an unreacted carboxylic acid derivative which is rich in the other enantiomer or diastereomer, or both of them, characterized in that the catalyst is an optically active compounds represented by the following general formula (C) or (D)

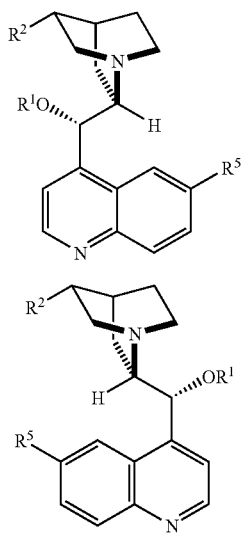

(C)

(D)

[wherein R¹ is a substituted or unsubstituted, saturated or unsaturated, straight-chain, branched or alicyclic aliphatic hydrocarbon group which can have a heteroatom, R² is ethyl or vinyl, and R⁵ is hydrogen or methoxy.].

The carboxylic acid derivative (A) to be used as a substrate, the optically active catalyst (C or D) and the nucleophile (Nu-H), which are important constituent elements of the present invention, are described in detail below.

The carboxylic acid derivative (A) is a cyclic compound (for example, a cyclic carbonate and a carbamate) derived from the racemic or diastereomeric mixture of the chiral carboxylic acid compounds, having at least one electrophilic reaction moiety to be attacked by the nucleophile in the presence of the catalyst and having at least one asymmetric carbon atom.

In the carboxylic acid derivatives represented by the general formula (A), when n is 1, two Rs are not the same, and when n is 2, two Rs are not the same at at least one of the adjacent two carbon atoms to which two Rs are linked. Namely, these Rs are selected respectively such that at least one of the carbon atoms to which two Rs are linked is asymmetric carbon.

In the present specification and claims, the saturated or unsaturated aliphatic hydrocarbon groups can be saturated aliphatic hydrocarbon group, namely, alkyl such as methyl, ethyl, propyl, isopropyl, butyl, isobutyl, t-butyl or pentyl, or aliphatic hydrocarbon groups having a carbon-carbon unsaturated group(s) such as a carbon-carbon double bond or a carbon-carbon triple bond, namely, alkenyl such as vinyl, allyl, isopropenyl, butenyl, isobutenyl or pentenyl, or alkynyl such as ethynyl, propynyl, butynyl or pentynyl.

In the present specification and claims, examples of substituents of the aliphatic hydrocarbon groups are groups and atoms generally known in organic chemistry such as halogen, hydroxy, alkoxy, carbonyl, acyl(alkanoyl and arylcarbonyl) alkoxy, ester (alkoxycarbonyl, aryloxycarbonyl and acyloxy), phosphoryl, phosphine, phosphonate, amine, amide, imine, thiol, thioether, thioester, sulfonyl, sulfate, sulfonate, nitrile, nitro, azo, azide, hydrazide, silyl and organic metals. The alkyl on the substituents of the aliphatic hydrocarbon groups can further have substituent(s). The aliphatic hydrocarbon groups can be groups having aromatic hydrocarbon group(s) such as aralkyl (for example, benzyl and phenethyl), aralkenyl or aralkynyl, or groups having heterocyclic group(s) such as pyridylmethyl.

In the present specification and claims, the expression "can have a heteroatom" means that at least one carbon atom(s) of the hydrocarbon group is replaced with heteroatom(s) such as nitrogen, oxygen, sulfur, phosphorus or selenium, or that heteroatom(s) is linked through a single bond or a multiple bond to at least one carbon atom of the hydrocarbon groups. Examples of the former are hydrocarbon groups (alkyl, aralkyl, alkylene, aralkylene and the like) having ether linkage, thioether linkage, —NH— linkage, sulfonyl linkage or the like. Examples of the latter are hydrocarbon groups having carbonyl, thiocarbonyl, ester, aldehyde, nitrile or the like.

A carbon number of the aliphatic hydrocarbon groups as R is preferably one to 30, more preferably one to 20. A member number of the alicyclic hydrocarbon groups is preferably three to ten, more preferably five to seven.

The aromatic hydrocarbon groups as R (including also aromatic hydrocarbon groups such as aralkyl, aralkenyl and aralkynyl) are monocyclic aromatic hydrocarbon groups having a member number of three to eight or polycyclic aromatic hydrocarbon groups formed by condensing two or more monocyclic aromatic hydrocarbon groups. Examples thereof are phenyl, naphthyl, phenancyl and anthranyl. Examples of substituents of the aromatic hydrocarbon groups can be the same as the above-mentioned substituents of the aliphatic hydrocarbon groups. The substituted aromatic hydrocarbon groups can be phenyl having alkyl, for example, tolyl or aromatic hydrocarbon groups substituted by a transition metal such as Fe (Fe can have organic group(s)), for example, a ferrocene ring group.

The heterocyclic groups as R can be not only aromatic but also nonaromatic so far as the groups have heteroatom(s) in their ring. The heteroatom(s) in the heterocyclic groups can be nitrogen, oxygen, sulfur, phosphorus, selenium or the like. The heterocyclic groups can have carbonyl in their ring.

Examples of aromatic heterocyclic groups are furyl, thienyl, imidazolyl, oxazolyl, pyridyl, pyrimidinyl, pyridazinyl, pyrazinyl and triazolyl. Examples of nonaromatic heterocyclic groups are so-called aliphatic heterocyclic compounds such as pyrrolidinyl, piperazinyl, tetrahydrofuryl, dihydrofuryl, 1,3-dithianyl, lactone and lactam. Examples of substituents of the heterocyclic groups are substituents exemplified as the substituents of the aliphatic hydrocarbon groups.

In the present specification and claims, the noncarbon substituents as R in the general formula (A) are groups containing at least one atom other than carbon (for example, a heteroatom such as nitrogen, oxygen, sulfur, phosphorus or selenium) and linked through this atom to carbon atom(s) of the five-membered ring or the six-membered ring of the general formula (A). Examples of substituents are hydroxy, alkoxy, phosphoryl, phosphine, phosphonate, amine, amide, imine, thiol, thioether, thioester, sulfonyl, sulfate, sulfonate, nitro, azo, azide, hydrazide, silyl, boron-containing groups and organic metal groups. The noncarbon atoms as R in the general formula (A) are monovalent atoms linked to carbon of the five-membered ring or the six-membered ring of the general formula (A) and are exemplified by a hydrogen atom and a halogen atom.

Examples of R' in X and Z are protecting groups of amino and amide described in the literature (Greene, T. W. et al. Protective groups in organic synthesis 2nd ed., United States, John Wiley & Sons, Inc., 1991, 309-405) such as acyl having one to 20 carbon atoms such as formyl, acetyl, propionyl or butyryl, sulfonyl such as mesyl or tosyl, oxycarbonyl such as benzyloxycarbonyl, tert-butyloxycarbonyl or allyloxycarbonyl, and aminocarbonyl such as phenylaminocarbonyl.

Typical examples of substrates; the racemates (A-1 to A-3) and the diastereomeric mixtures (A-4 and A-5); are represented by structural formulae below.

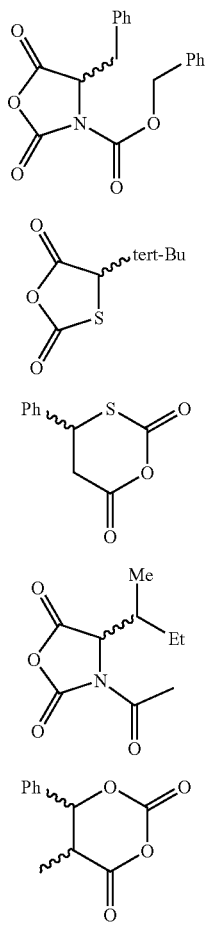

The catalysts to be used in the present invention are optically active amines represented by the general formula (C) or (D).

In the formulae (C) and (D), $R^1$ is a substituted or unsubstituted, saturated or unsaturated, straight-chain, branched or alicyclic aliphatic hydrocarbon group which can have a heteroatom, $R^2$ is ethyl or vinyl, and $R^5$ is hydrogen or methoxy group.

The substituted or unsubstituted, saturated or unsaturated, straight-chain, branched or alicyclic aliphatic hydrocarbon groups which can have a heteroatom as $R^1$ can have the same meaning as that described above about R of the general formula (A). The aliphatic hydrocarbon groups particularly can be alkyl such as methyl, ethyl, propyl, isopropyl, butyl, isobutyl, t-butyl or pentyl, or aliphatic hydrocarbon groups having a carbon-carbon unsaturated bond such as a carbon-carbon double bond or a carbon-carbon triple bond, namely, alkenyl such as vinyl, allyl, isopropenyl, butenyl, isobutenyl or pentenyl, or alkynyl such as ethynyl, propynyl, butynyl or pentynyl.

Examples of substituents of aliphatic hydrocarbon groups are groups and atoms generally known in organic chemistry such as halogen, hydroxy, alkoxy, carbonyl, acyl(alkanoly and arylcarbonyl)alkoxy, ester (alkoxycarbonyl, aryloxycarbonyl and acyloxy), phosphoryl, phosphine, phosphonate, amine, amide, imine, thiol, thioether, thioester, sulfonyl, sulfate, sulfonate, nitrile, nitro, azo, azide, hydrazide, silyl and organic metals. The alkyl on the substituents of the aliphatic hydrocarbon groups can further have substituent(s). The aliphatic hydrocarbon groups can be groups having aromatic hydrocarbon group(s) such as aralkyl (for example, benzyl and phenethyl), aralkenyl or aralkynyl, or groups having heterocyclic group(s) such as pyridylmethyl.

Preferred optically active compounds are compounds wherein $R^1$ is a substituted or unsubstituted, saturated or unsaturated, straight-chain, branched, alicyclic aliphatic hydrocarbon group having one to 20 carbon atoms, $R^2$ is ethyl or vinyl, and $R^5$ is hydrogen or methoxy in the above general formula (C) or (D).

Other preferred optically active compounds are compounds wherein $R^1$ is a group represented by the following general formula (G), (H), (J) or (K)

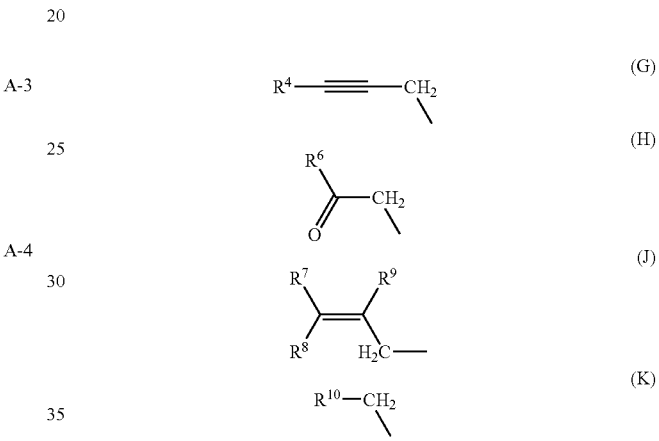

[wherein $R^4$, $R^6$, $R^7$, $R^8$, $R^9$ and $R^{10}$, the same or different, are substituted or unsubstituted, saturated or unsaturated, straight-chain, branched or alicyclic aliphatic hydrocarbon groups which can have heteroatom(s), substituted or unsubstituted aromatic hydrocarbon groups, substituted or unsubstituted heterocyclic groups, or noncarbon substituents or atoms.], $R^2$ is ethyl or vinyl, and $R^5$ is hydrogen or methoxy in the general formula (C) or (D).

The noncarbon substituents or atoms as $R^4$, $R^6$, $R^7$, $R^8$, $R^9$ and $R^{10}$ can have the same meanings as those described above about R of the general formula (A).

In the compounds of the general formula (C) or (D), compounds having the group of the general formula (G), (H), (J) or (K) as $R^1$, namely, compounds wherein $R^1$ has a methylene chain ($-CH_2-$) at the terminal of bond to O are easy to synthesize and tend to exhibit good enantiomer selectivity in optical resolution reactions. When $R^1$ contains an unsaturated bond or heteroatom(s), good enantiomer selectivity tends to be obtained, too.

Further other preferred optically active compounds are compounds wherein $R^1$ is methyl, ethyl, propyl, isopropyl, butyl, benzyl, allyl, propynyl, tert-butoxycarbonylmethyl, 2-methoxyethyl, 2-butynyl, iso-prop oxycarbonylmethyl, methoxycarbonylmethyl, o-methoxybenzyl, m-methoxybenzyl, p-methoxybenzyl, o-chlorobenzyl, m-chlorobenzyl, p-chlorobenzyl, 2-pyridylmethyl, 3-pyridylmethyl, 4-pyridylmethyl, 2-furylmethyl, 3-furylmethyl, 2-thienylmethyl, 3-thienylmethyl, 1-naphthylmethyl, 2-naphthylmethyl, prenyl, cinnamyl, methallyl, homoallyl, homobenzyl, aminocarbonylmethyl, N,N-diethylaminocarbonylmethyl, cyanomethyl, acetylmethyl, cyclopropylmethyl, 3-phenyl-2-propynyl, 3-methoxycarbonyl-2-propynyl or 3-methoxycarbonyl-2-propenyl, $R^2$ is ethyl or vinyl, and $R^5$ is hydrogen or methoxy in the formula (C) or (D).

$R^1$ in the above general formula (C) can be substituted alkyl represented by the following general formula (E), or $R^1$ in the above general formula (D) can be substituted alkyl represented by the following general formula (F).

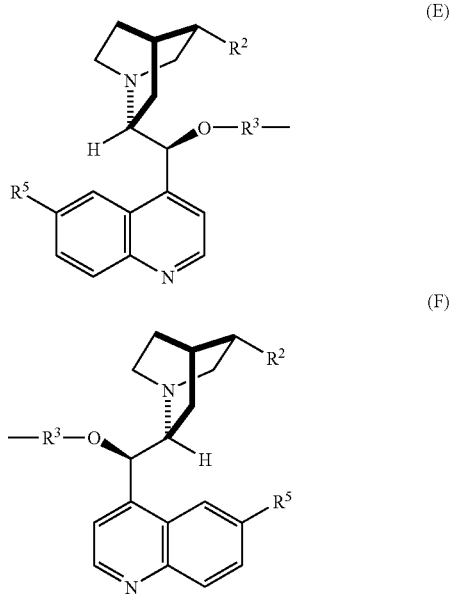

[wherein $R^2$ and $R^5$ have the same meanings as those defined about the formula (C). $R^3$ is a substituted or unsubstituted, saturated or unsaturated, straight-chain, branched or alicyclic divalent aliphatic hydrocarbon group which can have heteroatom(s).]

The divalent aliphatic hydrocarbon groups can be alkylene, alkylene having vinylene, groups having an aromatic hydrocarbon group such as aralkylene, divalent groups (-aliphatic hydrocarbon group-aromatic hydrocarbon group-aliphatic hydrocarbon group-), for example, (-alkylene-arylene-alkylene-), or groups having a heterocyclic group (-aliphatic hydrocarbon group-heterocyclic group-aliphatic hydrocarbon group).

Further other preferred optically active compounds are compounds wherein $R^3$ is ethylene, propylene, butylene, 2-butynylene, 2-butenylene, o-xylylene, m-xylylene, p-xylylene, 2,5-furylbismethylene, 3,4-furylbismethylene, 2,5-thienylbismethylene, 3,4-thienylbismethylene, 2,6-pyridylbismethylene, 3,5-pyridylbismethylene, 2,3-pyrazylbismethylene, 2,5-pyrazylbismethylene, 2,6-pyrazylbismethylene, 3,6-pyridazylbismethylene, 4,5-pyridazylbismethylene, 2-oxopropylene or 2,3-dioxobutylene in the formula (E) or (F).

In the general formula (C) and (D), dihydro compounds ($R^2$ is ethyl) of quinidine and quinine ($R^5$ is methoxy) exhibit reactivity and selectivity which are approximately equal to those of corresponding unsaturated compounds ($R^2$ is vinyl) of quinidine and quinine, but the unsaturated compounds are preferred to the dihydro compounds in terms of availability.

The optically active compounds represented by the general formulae (C) and (D) can be prepared, for example, by alkylating an alcohol moiety of corresponding quinine or quinidine or derivatives thereof with an electrophilic reagent such as an alkyl halide (so-called Williamson synthetic method) or the like. Solvents to be used are not particularly limited. Bipolar aprotic solvents such as DMF are preferable. The optically active compounds represented by the general formulae (C) and (D) thus obtained can also be further converted into the other optically active compounds represented by the general formulae (C) and (D). For example, O-propynyl can be converted into O-2-oxopropyl by hydration.

The above-mentioned optically active catalysts can also be supported on polymers or solids through a covalent bond formed at $R^1$ and/or $R^2$ in the general formulae (C) and (D) and insolubilized for use (Kobayashi et al. Tetrahedron Lett., 1980, 21, 2167-2170). The insolubilized catalysts can be easily recovered by filtration after reactions.

The amount of the catalyst to be used in the present invention is preferably 0.001 to 1,000 mol %, more preferably 0.01 to 500 mol %, further preferably 0.1 to 300 mol % to the substrate. When the amount is too small, enantiomer selectivity and a reaction rate is lowered. When the amount is too large, the catalyst is difficult to dissolve in the solvent. The catalysts can be easily extracted and separated with acidic aqueous solutions after reactions and can be recycled.

The nucleophiles (Nu-H) to be used in the present invention can be chemical species having reactive electron pairs and can be any of electrically neutral species, organic anions and inorganic anions. Examples of nucleophiles are nitrogen-containing nucleophiles (amines, amides, imides, ammonia, hydrazine, azides and the like), oxygen-containing nucleophiles (water, alcohols, a hydroxide ion, alkoxydes, siloxanes, carboxylates, peroxides and the like), sulfur-containing nucleophiles (mercaptanes, thiolates, bisulfites, thiocyanates and the like), carbon-containing nucleophiles (cyanides, malonates, acetylides, enolates, inolates, Grignard reagents, organocopper reagents, organozinc reagents, organolithium reagents and the like) and hydride anions. Amines, water, alcohols and thiols are preferable among them. Alcohols are the most preferable since it is easy to handle. In particular, primary alcohols are preferable from the standpoint of the reaction rate. Preferred alcohols are methanol, ethanol, n-propanol, n-butanol, benzyl alcohol, allyl alcohol, trifluoroethanol, cinnamyl alcohol and the like. Incorporating a nucleophile site into the substrate, kinetic resolution by an intramolecular reaction can be performed.

The amount of the nucleophile to be used in the present invention is preferably 10 to 1,000 mol %, more preferably 25 to 500 mol %, further preferably 40 to 200 mol % to the substrate. When the amount of the nucleophile is too small, optical purities of the one optically active nucleophile derivative (B) and the other optically active unreacted carboxylic acid derivative are sometimes insufficient. When the amount is too large, enantiomer selectivity tends to be lowered.

In the method of kinetic resolution in the present invention, when a substrate concentration is increased, the unit yield of the optically active substance increases, but the enantiomer selectivity is lowered. On the other hand, when the substrate concentration is lowered, the enantiomer selectivity is improved, but the unit yield of the optically active substance is lowered. The substrate concentration to perform optical resolution is preferably 0.0001 to 5.0 mol/l, more preferably 0.001 to 3.0 mol/l, further preferably 0.01 to 1.0 mol/l.

In the present invention, the addition order of the carboxylic acid derivative (A) as the substrate, the optically active catalyst (C and D) and the nucleophile (Nu-H) is not particularly limited so far as kinetic resolution is performed in a mixed solution using a means such as stirring, shaking or an ultrasonic wave. In general, a method wherein the nucleophile is added to the mixed solution of the substrate and the catalyst gives good results in terms of the enantiomer selectivity.

In the method of kinetic resolution in the present invention, generally the higher a reaction temperature, the shorter can be reaction time, but the enantiomer selectivity tends to be lowered. On the other hand, when the reaction temperature is low, the reaction time tends to become long, and the enantiomer selectivity tends to improve. Accordingly, though the reaction temperature changes depending on the combination of the substrate, the catalyst and the like to be used, the temperature is preferably −100° to 100° C., more preferably −90° to 70° C., further preferably −80° to 50° C.

It is preferable to perform the method of kinetic resolution in the present invention in the solvent. Preferred solvents are inert solvents which is not reacted with the substrates and the catalysts, and reaction liquids can be any of homogenous systems (the substrates and the catalysts are dissolved in the solvent) and heterogenous systems (at least a portion of the substrates and/or catalysts is insoluble). The homogenous systems are excellent in reaction rates. Examples of solvents are ether solvents (diethyl ether, dibutyl ether, 1,2-dimethoxyethane, diglyme, tert-butyl methyl ether (MTBE), tetrahydrofuran (THF), dioxane, cyclopropyl methyl ether and the like), halogenated hydrocarbon solvents (carbon tetrachloride, chloroform, dichloromethane, dichloroethane and the like), hydrocarbon solvents (hexane, pentane and the like), aromatic solvents (benzene, toluene, xylene, ethylbenzene, styrene, anisole, N,N-dimethylaniline, chlorobenzene, dichlorobenzene, methyl benzoate and the like), ester solvents (ethyl acetate and the like), ketone solvents (acetone, methyl ethyl ketone and the like) and aprotic polar solvents (acetonitrile, N,N-dimethylformamide, dimethylsulfoxide and the like). These are used solely or in combination. Among them, solvents having low polarity such as ether solvents and aromatic solvents are preferable since these solvents tend to exhibit high enantiomer selectivity. Solvents such as alcohols and amines which reacts with the substrates can also be used, if the solvents themselves work as the nucleophiles, or the reaction rates of the solvents with the substrates are sufficiently low. When the nucleophile is water or the hydroxide ion, solvents containing a proper amount of water or the hydroxide ion can also be used.

The aromatic solvents are preferable since the solvents tend to prevent the enantiomer selectivity from lowering even if the substrate concentration is increased. The aromatic solvent can be used in combination with other one or two or more solvents.

In the method of kinetic resolution in the present invention, ionic liquids, supercritical fluids and the like can also be used as solvents. Biphasic solvents such as emulsions and suspensions and lipid biphases can also be used as solvents. Further, the reaction can also be performed in a solid phase.

The method of kinetic resolution in the present invention can also be performed under an atmosphere of gases which are reactive with the nucleophiles such as an HCN gas. Partial pressure of this gas is preferably 0.1 to 1,000 atm, more preferably 0.5 to 100 atm, further preferably 1 to 10 atm.

The present invention also relates to novel optically active compounds represented by the above general formula (C) or (D). Definitions of the symbols in the formula (C) or (D) are as mentioned above. These optically active compounds are useful, for example, as the catalysts to be used for the above-mentioned method of optical resolution.

The recemic or diastereomeric mixture (A) of the chiral carboxylic acid derivatives as the substrate is reacted with the nucleophile (Nu-H) in the presence of the optically active catalyst, thereby obtaining the nucleophile derivative which is rich in one enantiomer or diastereomer, unreacted carboxylic acid derivative which is rich in the other enantiomer or diastereomer, or both of them. In the kinetic optical resolution, when a racemization rate of the other optically active unreacted carboxylic acid derivative is far higher than a formation reaction rate of the nucleophile derivative (B) which is rich in one enantiomer or diastereomer by the above-mentioned nucleophile, the formation reaction of the above-mentioned nucleophile derivative (B) which is rich in one enantiomer or diastereomer can be made proceed at the same time as racemization of the other optically active unreacted carboxylic acid derivative. In this case, only one optically active nucleophile derivative (B) can be formed in high optical purity and in a theoretical yield of 100% (so-called dynamic kinetic resolution; Noyori, R. et al. Bull. Chem. Soc. Jpn., 1995, 68, 36-55).

BEST MODE FOR CARRYING OUT THE INVENTION

The present invention is described by giving Examples below, but the present invention is not limited to these Examples.

Reactor and the Like

A reactor was flame-dried under a nitrogen atmosphere, and a substrate, a nucleophile, a catalyst, a solvent and the like were introduced into the reactor. MS4A (molecular sieve, 4A (powder): purchased from Aldrich Co., Ltd. in U.S.) was used which had been flame-dried under reduced pressure immediately before use.

Solvents

Diethyl ether, MTBE (tert-butyl methyl ether), THF (tetrahydrofuran) and toluene were used which had been distilled using benzophenone ketyl immediately before use.

Nucleophiles

Methanol (MeOH), ethanol (EtOH), allyl alcohol ($CH_2=CHCH_2OH$) and trifluoroethanol ($CF_3CH_2OH$) were used which had been distilled under drying with $CaH_2$.

Synthesis of Raw Materials

Phenylalanine, 4-chlorophenylalanine and 2-thienylalanine, which are α-racemic amino acids, were purchased from BACHEM Co., Ltd. in Switzerland. 2-Aminooctanoic acid, which is an α-racemic amino acid, and 3-aminobutanoic acid, which is a β-racemic amino acid, were purchased from Aldrich Co., Ltd. in U.S. 3-Phenyllactic acid and mandelic acid, which are α-racemic hydroxycarboxylic acids, were purchased from FLUKA Co., Ltd. in Switzerland. Five-membered ring derivatives (substrates (1)a, (1)b, (1)c and (1)d) derived from a -racemic amino acids were synthesized according to the literatures (Daly, W. H. et al., Tetrahedron Lett., 1988, 29, 5859-5862 and Fuller, W. D. et al., Biopolymers, 1996, 40, 183-205). A six-membered ring carboxylic acid derivative (N-tert-butyloxycarbonyl-4-methyl-4,5-dihydro-1,3-oxazin-2,6-dione (substrate (4)) derived from β-racemic amino acid was synthesized according to the literature (Mckiernan, M. et al., J. Org. Chem., 2001, 66, 6541-6544). 1,3-Dioxolane-2,4-dione derivatives (substrates (7)a and (7)b) derived from α-hydroxycarboxylic acids were synthesized according to the literature (Toyooka, K. et al., Heterocycles, 1989, 29, 975-978).

Structural formulae of the carboxylic acid derivatives as substrates are as follows.

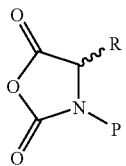

(1)a; R = CH$_2$Ph, P = Alloc
(1)b; R = CH$_2$—4-ClC$_6$H$_4$, P = Cbz
(1)c; R = 2-thienylmethyl, P = Cbz
(1)d; R = CH$_3$(CH$_2$)$_5$, P = Cbz

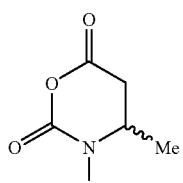

(4)

Alloc = allyloxycarbonyl
Cbz = benzyloxycarbonyl
Boc = butyloxycarbonyl

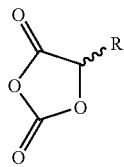

(7)a; R = CH$_2$Ph
(7)b; R = Ph

Catalysts

Quinidine, quinine, dihydroquinine, cinchonidine and (DHQD)$_2$AQN were purchased from Aldrich Co., Ltd. in U.S. These compounds were converted into the following Me-Q, Me-QD, Bn-Q, CH$_2$=CHCH$_2$-Q, Et-Q, HC≡CCH$_2$-Q, t-BuO$_2$CCH$_2$-Q, MeOCH$_2$CH$_2$-Q, HC CCH$_2$—HQ, HC≡CCH$_2$—CD, MeC≡CCH$_2$-Q, i-PrO$_2$CCH$_2$-Q, o-MeOC$_6$H$_4$CH$_2$-Q, o-ClC$_6$H$_4$CH$_2$-Q, 2-PyCH$_2$-Q, 2-FurCH$_2$-Q, 2-ThCH$_2$-Q, Me$_2$C=CHCH$_2$-Q, H$_2$NCOCH$_2$-Q, Et$_2$NCOCH$_2$-Q, NCCH$_2$-Q, cyclo-C$_3$H$_5$CH$_2$-Q, PhC≡CCH$_2$-Q, MeCOCH$_2$-Q, o-Q-CH$_2$C$_6$H$_4$CH$_2$-Q, Q-(CH$_2$)$_4$-Q, Q-CH$_2$C≡CCH$_2$-Q and HC≡CCH$_2$-QD, which are O-alkyl ether derivatives, to use them in Examples.

In Comparative Examples, quinidine, quinine, dihydroquinine and cinchonidine, whose alcohol moieties are free, and (DHQD)$_2$AQN, whose alcohol moiety is protected with aryl, were used.

All chemical purities of the catalysts before optical resolution reactions were 99% or higher according to $^1$H NMR analysis.

In the above-mentioned symbols of the catalysts, QD, Q, DHQ and CD mean quinidine, quinine, dihydroquinine and cinchonidine respectively (Kacprzak, K. et al., Synthesis, 2001, 961-998).

Examples of synthesis of O-alkyl ether derivatives are shown below. Other O-alkyl ether derivatives can be synthesized in a same manner as these Examples.

Synthesis of O-methylquinine (Me-Q)

NaH (0.52 g, 13 mmol, purity in mineral oil: 60%) was washed with hexane at room temperature under a nitrogen atmosphere, and then DMF (50 ml) was added to the NaH to give a suspension. Quinine (3.24 g, 11 mmol) was added to the suspension little by little, and the reaction mixture was stirred for two hours until it becomes a yellow transparent solution, followed by cooling to 0° C. Methyl iodide (1.42 g, 10 mmol) was added slowly to the solution, then the temperature of the reaction mixture was raised to room temperature, followed by stirring the mixture for one hour. The reaction mixture was cooled to 0° C. again, water (50 ml) was poured into the reaction mixture carefully, and toluene (50 ml) was added thereto. The aqueous and the organic layers were separated. The organic layer was washed with toluene (15 ml×3), and the organic layer combined with this toluene was washed with water (20 ml×5) and dried over anhydrous Na$_2$SO$_4$. The solvent was evaporated under reduced pressure, and the residue was purified by flash column chromatography (hexane:acetone:diethylamine=25:25:1) to give colorless viscous liquid O-methylquinine (1.62 g, yield: 44%). Chemical purity of Me-Q measured by $^1$H NMR analysis was 99% or higher.

$^1$H NMR (CDCl$_3$) δ: 1.45-1.60 (m, 1H), 1.70-1.80 (m, 4H), 2.20-2.30 (m, 1H), 2.55-2.80 (m, 2H), 3.05-3.15 (m, 2H), 3.31 (s, 3H), 3.35-3.45 (m, 1H), 3.94 (s, 3H), 4.85-5.00 (m, 3H), 5.65-5.80 (m, 1H), 7.31 (d, J=2.7 Hz, 1H), 7.37 (dd, J=9.2, 2.7 Hz, 1H), 7.41 (d, J=4.6 Hz, 1H), 8.04 (d, J=9.2 Hz, 1H), 8.76 (d, J=4.3 Hz, 1H).

Synthesis of O-methylquinidine (Me-QD)

Colorless viscous liquid O-methylquinidine was synthesized (1.76 g, yield: 52%) in the same manner as that of the synthesis of Me-Q except that quinine was changed to quinidine. Chemical purity of Me-QD measured by $^1$H NMR analysis was 99% or higher.

$^1$H NMR (CDCl$_3$) δ: 1.10-1.25 (m, 1H), 1.40-1.60 (m, 2H), 1.70-1.80 (m, 1H), 2.00-2.35 (m, 2H), 2.70-3.05 (m, 4H), 3.25-3.35 (m, 1H), 3.32 (s, 3H), 3.93(s, 3H), 5.05-5.12 (m, 3H), 6.02-6.15 (m, 1H), 7.29 (d, J=2.7 Hz, 1H), 7.37 (dd, J=9.2, 3.0 Hz, 1H), 7.42 (d, J=4.3 Hz, 1H), 8.04 (d, J=9.2 Hz, 1H), 8.75 (d, J=4.6 Hz, 1H).

Synthesis of O-benzylquinine (Bn-Q)

Colorless viscous liquid O-benzylquinine was synthesized (2.69 g, yield: 65%) in the same manner as that of synthesis of Me-Q except that methyl iodide was changed to benzyl chloride. Chemical purity of Bn-Q measured by $^1$H NMR analysis was 99% or higher.

$^1$H NMR (CDCl$_3$) δ: 1.40-1.90 (m, 5H), 2.15-2.32 (m, 1H), 2.50-2.70 (m, 2H), 3.00-3.20 (m, 2H), 3.30-3.50 (m, 1H), 3.91 (s, 3H), 4.37-4.48 (m, 2H), 4.88-5.20 (m, 2H), 5.20 (d, J=1.5 Hz, 1H), 5.67-5.83 (m, 1H), 7.28-7.41 (m, 7H), 7.47 (d, J=4.6 Hz, 1H), 8.06 (d, J=9.2 Hz, 1H), 8.76 (d, J=4.3 Hz, 1H).

Synthesis of O-allylquinine (CH$_2$=CHCH$_2$-Q)

Colorless viscous liquid O-allylquinine was synthesized (2.84 g, yield: 78%) in the same manner as that of the synthesis of Me-Q except that methyl iodide was changed to allyl chloride. Chemical purity of CH$_2$=CHCH$_2$-Q measured by $^1$H NMR analysis was 99% or higher.

$^1$H NMR (CDCl$_3$) δ: 1.45-1.65 (m, 2H), 1.70-1.87 (m, 3H), 2.19-2.35 (m, 1H), 2.55-2.73 (m, 2H), 3.06-3.20 (m, 2H), 3.35-3.53 (m, 1H), 3.80-4.02 (m, 2H), 3.93 (s, 3H), 4.88-4.98 (m, 2H), 5.13-5.34 (m, 3H), 5.67-5.80 (m, 1H), 5.88-6.02 (m, 1H), 7.31 (d, J=2.3 Hz, 1H), 7.37 (dd, J=9.2, 2.6 Hz, 1H), 7.44 (d, J=4.3 Hz, 1H), 8.04 (d, J=9.2 Hz, 1H), 8.75 (d, J=4.3 Hz, 1H).

Synthesis of O-ethylquinine (Et-Q)

Colorless viscous liquid O-ethylquinine was synthesized (2.04 g, yield: 58%) in the same manner as that of the synthesis of Me-Q except that methyl iodide was changed to ethyl bromide. Chemical purity of Et-Q measured by $^1$H NMR was 99% or higher.

$^1$H NMR (CDCl$_3$) δ: 1.24 (t, J=6.8 Hz, 3H), 1.45-1.60 (m, 2H), 1.70-1.90 (m, 3H), 2.20-2.34 (m, 1H), 2.55-2.80 (2H), 3.05-3.16 (m, 2H), 3.36-3.52 (m, 3H), 3.93 (s, 3H), 4.86-4.97 (m, 2H), 5.06 (d, J=3.6 Hz, 1H), 5.66-5.79. (m, 1H), 7.31 (d, J=2.3 Hz, 1H), 7.37 (dd, J=9.1, 2.8 Hz, 1H), 7.44 (d, J=4.3 Hz, 1H), 8.03 (d, J=9.1 Hz, 1H), 8.74 (d, J=4.3 Hz, 1H).

Synthesis of O-propylquinine (CH≡CCH$_2$-Q)

Colorless viscous liquid O-propylquinine was synthesized (2.47 g, yield: 62%) in the same manner as that of the synthesis of Me-Q except that methyl iodide was changed to propynyl bromide. Chemical purity of CH≡CCH$_2$-Q measured by $^1$H NMR analysis was 99% or higher.

$^1$H NMR (CDCl$_3$) δ: 1.42-1.82 (m, 5H), 2.20-2.33 (m, 1H), 2.46 (t, J=2.4 Hz, 1H), 2.56-2.72 (m, 2H), 3.04-3.24 (m, 2H), 3.35-3.50 (m, 1H), 3.87-3.95 (m, 1H), 3.94 (s, 3H), 4.22 (dd, J=15.9, 2.4 Hz, 1H), 4.89-4.99 (m, 2H), 5.33 (d, J=4.3 Hz, 1H), 5.69-5.82 (m, 1H), 7.36-7.43 (m, 3H), 8.04 (d, J=9.7 Hz, 1H), 8.76 (d, J=4.6 Hz, 1H).

Synthesis of O-(tert-butoxycarbonylmethyl)quinine (t-BuO$_2$CCH$_2$-Q)

Colorless viscous liquid O-(tert-butoxycarbonylmethyl)quinine was synthesized (2.36 g, yield: 49%) in the same manner as that of the synthesis of Me-Q except that methyl iodide was changed to tert-butyl chloroacetate. Chemical purity of t-BuO$_2$CCH$_2$-Q measured by $^1$H NMR was 99% or higher.

$^1$H NMR (CDCl$_3$) δ: 1.40-1.95 (m, 4H), 1.44 (s, 9H), 2.20-2.32 (m, 2H), 2.55-2.80 (m, 2H), 3.03-3.23 (m, 2H), 3.45-3.60 (m, 1H), 3.75 (d, J=16.2 Hz, 1H), 3.94 (s, 3H), 3.96 (d, J=16.2 Hz, 1H), 4.90-4.99 (m, 2H), 5.21-5.35 (brs, 1H), 5.69-5.82 (m, 1H), 7.30-7.47 (m, 3H), 8.04 (d, J=9.5 Hz, 1H), 8.75 (d, J=4.6 Hz, 1H).

Synthesis of O-(2-methoxyethyl)quinine (MeOCH$_2$CH$_2$-Q)

Colorless viscous liquid O-(2-methoxyethyl)quinine was synthesized (2.14 g, yield: 51%) in the same manner as that of the synthesis of Me-Q except that methyl iodide was changed to 2-methoxyethyl chloride. Chemical purity of MeOCH$_2$CH$_2$-Q measured by $^1$H NMR analysis was 99% or higher.

$^1$H NMR (CDCl$_3$) δ: 1.45-1.85 (m, 4H), 2.05-2.33 (m, 2H), 2.55-2.75 (m, 2H), 3.06-3.14 (m, 2H), 3.32-3.60 (m, 5H), 3.36 (s, 3H), 3.94 (s, 3H), 4.87-4.98 (m, 2H), 5.13 (d, J=3.2 Hz, 1H), 5.67-5.79 (m, 1H), 7.33 (brs, 1H), 7.37 (dd, J=8.9, 2.7 Hz, 1H), 7.47 (d, J=4.6 Hz, 1H), 8.03 (d, J=9.2 Hz, 1H), 8.75 (d, J=4.6 Hz, 1H).

Synthesis of O-propynyldihydroquinine (CH≡CCH$_2$-DHQ)

Colorless viscous liquid O-propynyldihydroquinine was synthesized (2.84 g, yield: 71%) in the same manner as that of the synthesis of Me-Q except that methyl iodide and quinine were changed to propynyl bromide and dihydroquinine. Chemical purity of CH≡CCH$_2$-DHQ measured by $^1$H NMR analysis was 99% or higher.

$^1$H NMR (CDCl$_3$) δ: 1.42-2.00 (m, 10H), 2.30-2.35 (m, 2H), 2.46 (t, J=2.4 Hz, 1H), 3.04-3.24 (m, 2H), 3.35-3.50 (m, 2H), 3.87-3.95 (m, 1H), 3.96 (s, 3H), 4.22 (dd, J=15.6, 2.4 Hz, 1H), 5.69-5.82 (m, 1H), 7.36-7.43 (m, 3H), 8.04 (d, J=9.7 Hz, 1H), 8.76 (d, J=4.6 Hz, 1H).

Synthesis of O-propynylcinchonidine (CH≡CCH$_2$—CD)

Colorless viscous liquid O-propynylcinchonidine was synthesized (2.56 g, yield: 70%) in the same manner as that of the synthesis of Me-Q except that methyl iodide and quinine were changed to propynyl bromide and cinchonidine. Chemical purity of CH≡CCH$_2$—CD measured by $^1$H NMR analysis was 99% or higher.

$^1$H NMR (CDCl$_3$) δ: 1.42-1.82 (m, 5H), 2.20-2.33 (m, 1H), 2.46 (t, J=2.2 Hz, 1H), 2.56-2.72 (m, 2H), 3.04-3.24 (m, 2H), 3.35-3.50 (m, 1H), 3.91 (dd, J=16.2, 2.4 Hz, 1H), 4.23 (dd, J=16.2, 2.2 Hz, 1H), 4.89-4.99 (m, 2H), 5.48-5.50 (m, 1H), 5.69-5.82 (m, 1H), 7.43-7.59 (m, 3H), 8.14-8.18 (m, 2H), 8.91 (d, J=4.1 Hz, 1H).

Synthesis of O-(2-butynyl)quinine (MeC≡CCH$_2$-Q)

Colorless viscous liquid O-(2-butynyl)quinine was synthesized (3.23 g, yield: 78%) in the same manner as that of the synthesis of Me-Q except that methyl iodide was changed to 1-bromo-2-butyne. Chemical purity of MeCH≡CCH$_2$-Q measured by $^1$H NMR analysis was 99% or higher.

$^1$H NMR (CDCl$_3$) δ: 1.30-2.30 (m, 6H), 1.83 (s, 3H), 2.56-2.72 (m, 2H), 3.04-3.24 (m, 2H), 3.35-3.60 (m, 1H), 3.87-3.95 (m, 1H), 3.95 (s, 3H), 4.16 (dd, J=15.9, 2.4 Hz, 1H), 4.89-4.99 (m, 2H), 5.30-5.40 (m, 1H), 5.69-5.80 (m, 1H), 7.36-7.43 (m, 3H), 8.03 (d, J=10.0, 1H), 8.75 (d, J=4.6 Hz, 1H).

Synthesis of O-(iso-propoxycarbonylmethyl)quinine (i-PRO$_2$CCH$_2$-Q)

Colorless viscous liquid O-(iso-propoxycarbonylmethyl)quinine was synthesized (2.33 g, yield: 50%) in the same manner as that of the synthesis of Me-Q except that methyl iodide was changed to iso-propyl bromoacetate. Chemical purity of i-PrO$_2$CCH$_2$-Q measured by $^1$H NMR analysis was 99% or higher.

$^1$H NMR (CDCl$_3$) δ: 1.21 (d, J=1.9, 3H), 1.24 (d, J=1.6, 3H), 1.42-1.82 (m, 5H), 2.20-2.40 (m, 1H), 2.56-2.72 (m, 2H), 3.04-3.24 (m, 2H), 3.35-3.60 (m, 1H), 3.85 (d, J=16, 1H), 3.96 (s, 3H), 4.05 (d, J=16, 1H), 4.90-5.00 (m, 2H), 5.02-5.10 (m, 1H), 5.20-5.35 (m, 1H), 5.69-5.82 (m, 1H), 7.30-7.43 (m, 3H), 8.04 (d, J=9.7 Hz, 1H), 8.76 (d, J=4.6 Hz, 1H).

Synthesis of O-(o-methoxybenzyl)quinine (o-MeOC$_6$H$_4$CH$_2$-Q)

Colorless viscous liquid O-(o-methoxybenzyl)quinine was synthesized (3.56 g, yield: 73%) in the same manner as that of the synthesis of Me-Q except that methyl iodide was changed to o-methoxybenzyl bromide. Chemical purity of o-MeOC$_6$H$_4$CH$_2$-Q measured by $^1$H NMR analysis was 99% or higher.

$^1$H NMR (CDCl$_3$) δ: 1.42-1.82 (m, 5H), 2.20-2.40 (m, 1H), 2.56-2.72 (m, 2H), 3.04-3.24 (m, 2H), 3.35-3.60 (m, 1H), 3.71 (s, 3H), 3.93 (s, 3H), 4.48 (s, 2H), 4.88-4.97 (m, 2H), 5.2-5.3 (m, 1H), 5.69-5.82 (m, 1H), 6.84 (d, J=8.4, 1H), 6.98 (t, J=7.6, 1H), 7.36-7.4 (m, 5H), 8.05 (d, J=9.7 Hz, 1H), 8.74 (d, J=4.6 Hz, 1H).

Synthesis of O-(o-chlorobenzyl)quinine (o-ClC$_6$H$_4$CH$_2$-Q)

Colorless viscous liquid O-(o-chlorobenzyl)quinine was synthesized (4.49 g, yield: 91%) in the same manner as that of the synthesis of Me-Q except that methyl iodide was changed to o-chlorobenzyl chloride. Chemical purity of o-ClC$_6$H$_4$CH$_2$-Q measured by $^1$H NMR analysis was 99% or higher.

$^1$H NMR (CDCl$_3$) δ: 1.42-2.40 (m, 5H), 2.20-2.30 (m, 1H), 2.56-2.72 (m, 2H), 3.04-3.24 (m, 2H), 3.35-3.60 (m, 1H), 3.95 (s, 3H), 4.48-4.59 (m, 2H), 4.90-5.00 (m, 2H), 5.20-5.35 (m, 1H), 5.69-5.82 (m, 1H), 7.30-7.43 (m, 7H), 8.06 (d, J=9.5 Hz, 1H), 8.76 (d, J=4.6 Hz, 1H).

Synthesis of O-(2-pyridinylmethyl)quinine (2-PyCH$_2$-Q)

Colorless viscous liquid O-(2-pyridinylmethyl)quinine was synthesized (3.65 g, yield: 80%) in the same manner as that of the synthesis of Me-Q except that methyl iodide was changed to 2-bromomethylpyridine hydrobromide. Chemical purity of 2-PyCH$_2$-Q measured by $^1$H NMR analysis was 99% or higher.

$^1$H NMR (CDCl$_3$) δ: 1.42-1.98 (m, 5H), 2.20-2.30 (m, 1H), 2.56-2.72 (m, 2H), 3.04-3.24 (m, 2H), 3.35-3.50 (m, 1H), 3.94 (s, 3H), 4.57 (s, 2H), 4.90-5.00 (m, 2H), 5.20-5.35 (m,

1H), 5.69-5.82 (m, 1H), 7.30-7.65 (m, 5H), 7.73 (td, J=8.1, 1.6, 1H), 8.05 (d, J=9.5 Hz, 1H), 8.53 (d, J=4.6, 1H), 8.74 (d, J=4.3 Hz, 1H).

Synthesis of O-(2-furylmethyl)quinine (2-FurCH$_2$-Q)

Colorless viscous liquid O-(2-furylmethyl)quinine was synthesized (0.44 g, yield: 10%) in the same manner as that of the synthesis of Me-Q except that methyl iodide was changed to 2-furylmethyl mesylate. Chemical purity of 2-FurCH$_2$-Q measured by $^1$H NMR analysis was 99% or higher.

$^1$H NMR (CDCl$_3$) δ: 1.42-1.98 (m, 5H), 2.20-2.30 (m, 1H), 2.56-2.72 (m, 2H), 3.04-3.24 (m, 2H), 3.35-3.50 (m, 1H), 3.93 (s, 3H), 4.29 (d, J=13 Hz, 1H), 4.46 (d, J=13 Hz, 1H), 4.90-5.00 (m, 2H), 5.20-5.25 (m, 1H), 5.69-5.82 (m, 1H), 6.22 (d, J=3.3 Hz, 1H), 6.31-6.32 (m, 1H), 7.30-7.49 (m, 4H), 8.05 (d, J=9.5 Hz, 1H), 8.77 (d, J=4.6 Hz, 1H).

Synthesis of O-(2-thienylmethyl)quinine (2-ThCH$_2$-Q)

Pale yellow viscous liquid O-(2-thienylmethyl)quinine was synthesized (0.46 g, yield: 10%) in the same manner as that of the synthesis of Me-Q except that methyl iodide was changed to 2-thienylmethyl mesylate. Chemical purity of 2-ThCH$_2$-Q measured by $^1$H NMR analysis was 99% or higher.

$^1$H NMR (CDCl$_3$) δ: 1.42-1.98 (m, 5H), 2.20-2.30 (m, 1H), 2.56-2.72 (m, 2H), 3.04-3.24 (m, 2H), 3.35-3.50 (m, 1H), 3.92 (s, 3H), 4.51 (d, J=12 Hz, 1H), 4.65 (d, J=12 Hz, 1H), 4.90-5.00 (m, 2H), 5.20-5.25 (m, 1H), 5.69-5.82 (m, 1H), 6.88 (d, J=3.0 Hz, 1H), 6.95-6.98 (m, 1H), 7.30-7.49 (m, 4H), 8.05 (d, J=9.2 Hz, 1H), 8.78 (d, J=4.3 Hz, 1H).

Synthesis of O-(3-methyl-2-butenyl)quinine (Me$_2$C=CHCH$_2$-Q)

Pale yellow viscous liquid O-(3-methyl-2-butenyl)quinine was synthesized (2.80 g, yield: 65%) in the same manner as that of the synthesis of Me-Q except that methyl iodide was changed to 1-chloro-3-methyl-2-butene. Chemical purity of Me$_2$C=CHCH$_2$-Q measured by $^1$H NMR analysis was 99% or higher.

$^1$H NMR (CDCl$_3$) δ: 1.50 (s, 3H), 1.77 (s, 3H), 1.42-1.90 (m, 5H), 2.20-2.30 (m, 1H), 2.56-2.72 (m, 2H), 3.04-3.24 (m, 2H), 3.35-3.50 (m, 1H), 3.92-4.01 (m, 2H), 3.94 (s, 3H), 4.90-5.00 (m, 2H), 5.10-5.25 (m, 1H), 5.34-5.39 (m, 1H), 5.69-5.82 (m, 1H), 7.30-7.43 (m, 3H), 8.04 (d, J=9.5 Hz, 1H), 8.75 (d, J=4.3 Hz, 1H).

Synthesis of O-aminocarbonylmethylquinine (NH$_2$COCH$_2$-Q)

Pale yellow viscous liquid O-aminocarbonylmethylquinine was synthesized (0.42 g, yield: 10%) in the same manner as that of the synthesis of Me-Q except that methyl iodide was changed to 2-bromoacetamide. Chemical purity of NH$_2$COCH$_2$-Q measured by $^1$H NMR analysis was 99% or higher.

$^1$H NMR (CDCl$_3$) δ: 1.42-2.40 (m, 4H), 2.20-2.30 (m, 1H), 2.61-2.82 (m, 3H), 3.04-3.14 (m, 1H), 3.20-3.41 (m, 2H), 3.88 (S, 2H), 3.94 (s, 3H), 4.90-5.00 (m, 2H), 5.10-5.20 (m, 1H), 5.69-5.78 (m, 1H), 7.30-7.43 (m, 3H), 8.06 (d, J=9.2 Hz, 1H), 8.76 (d, J=4.3 Hz, 1H).

Synthesis of O-(N,N-diethylaminocarbonylmethyl)quinine (Et$_2$NCO CH$_2$-Q)

Pale yellow viscous liquid O-(N,N-diethylaminocarbonylmethyl)quinine was synthesized (4.61 g, yield: 96%) in the same manner as that of the synthesis of Me-Q except that methyl iodide was changed to 2-chloro-N,N-diethylacetamide. Chemical purity of Et$_2$NCOCH$_2$-Q measured by $^1$H NMR analysis was 99% or higher.

$^1$H NMR (CDCl$_3$) δ: 0.99 (t, J=7.3, 3H), 1.10 (t, J=6.8, 3H), 1.42-2.10 (m, 6H), 2.20-2.30 (m, 1H), 2.61-2.82 (m, 2H), 3.07 (q, J=7.0 Hz, 2H), 3.04-3.50 (m, 2H), 3.40 (q, J=7.0 Hz, 2H), 3.86-3.91 (m, 2H), 3.96 (s, 3H), 4.90-5.00 (m, 2H), 5.10-5.30 (m, 1H), 5.73-5.86 (m, 1H), 7.36-7.45 (m, 3H), 8.04 (d, J=9.2 Hz, 1H), 8.76 (d, J=4.3 Hz, 1H).

Synthesis of O-cyanomethylquinine (NCCH$_2$-Q)

Pale yellow viscous liquid O-cyanomethylquinine was synthesized (1.24 g, yield: 30%) in the same manner as that of the synthesis of Me-Q except that methyl iodide was changed to chloroacetonitrile. Chemical purity of NCCH$_2$-Q measured by $^1$H NMR analysis was 99% or higher.

$^1$H NMR (CDCl$_3$) δ: 1.42-1.82 (m, 5H), 2.20-2.33 (m, 1H), 2.56-2.72 (m, 2H), 3.04-3.24 (m, 1H), 3.35-3.50 (m, 2H), 3.96-3.98 (m, 1H), 3.96 (s, 3H), 4.30 (d, J=16 Hz, 1H), 4.95-5.02 (m, 2H), 5.28-5.35 (m, 1H), 5.69-5.82 (m, 1H), 7.26-7.43 (m, 3H), 8.06 (d, J=9.2 Hz, 1H), 8.78 (d, J=4.1 Hz, 1H).

Synthesis of O-cyclopropylmethylquinine (cyclo-C$_3$H$_5$CH$_2$-Q)

Colorless viscous liquid O-cyclopropylmethylquinine was synthesized (4.07 g, yield: 98%) in the same manner as that of the synthesis of Me-Q except that methyl iodide was changed to bromomethylcyclopropane. Chemical purity of cyclo-C$_3$H$_5$CH$_2$-Q measured by $^1$H NMR analysis was 99% or higher.

$^1$H NMR (CDCl$_3$) δ: 0.12-0.18 (m, 2H), 0.49-0.53 (m, 2H), 1.42-2.40 (m, 6H), 2.20-2.30 (m, 1H), 2.56-2.72 (m, 2H), 3.04-3.25 (m, 4H), 3.35-3.50 (m, 1H), 3.94 (s, 3H), 4.90-5.00 (m, 2H), 5.00-5.23 (m, 1H), 5.69-5.82 (m, 1H), 7.30-7.43 (m, 3H), 8.03 (d, J=9.2 Hz, 1H), 8.75 (d, J=4.3 Hz, 1H).

Synthesis of O-(3-phenyl-2-propynyl)quinine (PhC≡CCH$_2$-Q)

Colorless viscous liquid O-(3-phenyl-2-propynyl)quinine was synthesized (3.23 g, yield: 78%) in the same manner as that of the synthesis of Me-Q except that methyl iodide was changed to 1-bromo-3-phenyl-2-propyne. Chemical purity of PhC≡CCH$_2$-Q measured by $^1$H NMR analysis was 99% or higher.

$^1$H NMR (CDCl$_3$) δ: 1.30-1.80 (m, 5H), 2.21-2.30 (m, 1H), 2.56-2.72 (m, 2H), 3.04-3.24 (m, 2H), 3.35-3.60 (m, 1H), 3.89 (s, 3H), 4.15 (d, J=15.6 Hz, 1H), 4.43 (d, J=15.6 Hz, 1H), 4.89-4.99 (m, 2H), 5.30-5.40 (m, 1H), 5.69-5.80 (m, 1H), 7.26-7.36 (m, 7H), 7.48, (d, J=4.3 Hz, 1H), 8.04 (d, J=9.2 Hz, 1H), 8.77 (d, J=4.6 Hz, 1H).

Synthesis of O-(2-oxopropyl)quinine (MeCOCH$_2$-Q)

O-Propynylquinine (HC≡CCH$_2$-Q) (228 mg, 0.63 mmol) was dissolved in a 20% sulfuric acid (0.5 g) solution, mercury oxide (9.1 mg, 0.042 mmol) was added to the solution, and the mixture was stirred at room temperature for 10 minutes. The mixture was further stirred at 70° C. for two hours and then cooled to 0° C., and a 2 N NaOH (3 ml) solution was added dropwise to the reaction mixture carefully. The aqueous and organic layers were separated, and the aqueous layer was extracted with ether (20 ml). The organic layer was combined with the extract, washed with water (3 ml) and dried over magnesium sulfate. After filtration, the solvent was evaporated under reduced pressure, and the residue was purified by column chromatography (hexane:acetone:diethylamine=25:25:1) to give colorless viscous O-(2-oxopropyl)quinine (194 mg, yield: 81%). Chemical purity of MeCOCH$_2$-Q measured by $^1$H NMR was 99% or higher.

$^1$H NMR (CDCl$_3$) δ: 1.40-1.82 (m, 5H), 2.17-2.33 (m, 1H), 2.19 (s, 3H), 2.55-2.71 (m, 2H), 3.04-3.25 (m, 2H), 3.33-3.50 (m, 1H), 3.87-3.95 (m, 1H), 3.93 (s, 3H), 4.22 (d, J=16.3 Hz,

1H), 4.89-4.98 (m, 2H), 5.31 (d, J=4.4 Hz, 1H), 5.70-5.82 (m, 1H), 7.36-7.43 (m, 3H), 8.04 (d, J=9.8 Hz, 1H), 8.75 (d, J=4.6 Hz, 1H).

Synthesis of O-propynylquinidine (HC≡CCH$_2$-QD)

Colorless viscous liquid O-propynylquinidine was synthesized (2.47 g, yield: 62%) in the same manner as that of the synthesis of Me-QD except that methyl iodide was changed to propynyl bromide. Chemical purity of HC≡CCH$_2$-QD measured by $^1$H NMR analysis was 99% or higher.

$^1$H NMR (CDCl$_3$) δ: 1.20-1.40 (m, 1H), 1.43-1.60 (m, 2H), 1.72-1.83 (m, 1H), 2.00-2.13 (m, 1H), 2.18-2.34 (m, 1H), 2.46 (t, J=2.4 Hz, 1H), 2.70-2.97 (m, 3H), 3.04-3.16 (m, 1H), 3.21-3.35 (m, 1H), 3.87-3.95 (m, 1H), 3.93 (s, 3H), 4.24 (dd, J=16.0, 2.3 Hz, 1H), 5.05-5.16 (m, 2H), 5.36 (d, J=4.0 Hz, 1H), 6.02-6.17 (m, 1H), 7.33-7.45 (m, 3H), 8.03 (d, J=9.8 Hz, 1H), 8.77 (d, J=4.5 Hz, 1H).

Synthesis of o-bisquininoxyxylene (o-Q-Xy-Q)

Pale yellow viscous liquid o-bisquininoxyxylene was synthesized (565 mg, yield: 15%) in the same manner as that of the synthesis of Me-Q except that methyl iodide was changed to o-xylylene dichloride (875 mg, 5 mmol). Chemical purity of o-Q-Xy-Q measured by $^1$H NMR analysis was 99% or higher.

$^1$H NMR (CDCl$_3$) δ: 0.80-1.90 (m, 10H), 2.10-2.30 (m, 2H), 2.47-2.60 (m, 4H), 2.93-3.28 (m, 6H), 3.88 (S, 6H), 4.36 (s, 4H), 4.87-4.95 (m, 4H), 5.05 (brs, 2H), 5.61-5.75 (m, 2H), 7.27-7.48 (m, 10H), 8.04 (d, J=9.2 Hz, 2H), 8.69 (d, J=4.1 Hz, 2H).

Synthesis of 1,4-bisquininoxybutane (Q-(CH$_2$)$_4$-Q)

Pale yellow viscous liquid 1,4-bisquininoxybutane was synthesized (0.35 g, yield: 10%) in the same manner as that of the synthesis of Me-Q except that methyl iodide was changed to 1,4-butanediol bismesylate (1.23 g, 5 mmol). Chemical purity of Q-(CH$_2$)$_4$-Q measured by $^1$H NMR analysis was 99% or higher.

$^1$H NMR (CDCl$_3$) δ: 1.42-1.62 (m, 4H), 1.71-1.89 (m, 10H), 2.20-2.33 (m, 2H), 2.56-2.72 (m, 4H), 3.04-3.24 (m, 4H), 3.31-3.52 (m, 6H), 3.94 (S, 6H), 4.95-5.02 (m, 4H), 5.02-5.18 (m, 2H), 5.64-5.71 (m, 2H), 7.18-7.40 (m, 6H), 8.03 (d, J=9.2 Hz, 2H), 8.74 (d, J=4.1 Hz, 2H).

Synthesis of 1,4-bisquininoxy-2-butyne (Q-CH$_2$C≡CCH$_2$-Q)

Pale yellow viscous liquid 1,4-bisquininoxy-2-butyne was synthesized (0.23 g, yield: 3%) in the same manner as that of the synthesis of Me-Q except that methyl iodide was changed to 2-butyne-1,4-diol bismesylate (1.21 g, 5 mmol). Chemical purity of Q-CH$_2$C≡CCH$_2$-Q measured by $^1$H NMR analysis was 99% or higher.

$^1$H NMR (CDCl$_3$) δ: 1.45-1.66 (m, 10H), 2.20-2.33 (m, 2H), 2.76-2.84 (m, 4H), 3.10-3.29 (m, 6H), 3.96 (s, 6H), 4.10-4.80 (br, 4H), 4.94-5.05 (m, 6H), 5.72-5.82 (m, 2H), 7.36-7.42 (m, 4H), 7.66 (d, J=2.7 Hz, 2H), 8.04 (d, J=9.2 Hz, 2H), 8.74 (d, J=4.3 Hz, 2H).

Instrumental Analysis

Optical purity (enantiomer excess) was calculated according to the following equation from each enantiomer ratio measured with an LC-6A type high performance liquid chromatograph (HPLC) manufactured by Shimazu Seisakusho, Ltd. and Chiralsel AS, OJ and OD columns (250×4.6 mm) manufactured by Daicell Co., Ltd.

Enantiomer excess (ee, %) = {Absolute value of [(enantiomer R) − (enantiomer S)] / [(enantiomer R) + (enantiomer S)]} × 100

Conversion (c) was measured with a GC-14A type gas-liquid chromatograph (GLC) manufactured by Shimazu Seisakusho, Ltd. and an HP-5 column manufactured by Hewlett-Packed Co., Ltd. in U.S.

s values, which are efficiency indexes of kinetic optical resolution, were calculated according to the following equation.

$$s = k(\text{fast})/k(\text{slow})$$
$$= \ln[1 - c(1 + ee)] / \ln[1 - c(1 - ee)]$$

(c=conversion, ee=enantiomer excess. Namely, enantiomer excess of one optically active nucleophile derivative (B) obtained by a reaction of a substrate with a nucleophile, for example, an optically active amino acid ester (R-2a) obtained in Example 1, corresponding esters obtained in Examples 2 to 33 and Comparative Examples 1 to 9, an ester (S-5) obtained in Example 34 and Comparative Example 10 or an ester (S-8a) obtained in Example 35 and Comparative Example 11.)

The larger the s value, the higher is enantiomer selectivity.

Since Examples 36 and 37 and Comparative Example 12 are examples of dynamic kinetic optical resolution, an s value of an obtained ester (S-8b) cannot be calculated. However, enantiomer selectivity can be compared by comparing optical purity of the ester (S-8b).

Chemical purity of recovered catalysts was calculated from proton ratios of $^1$H NMR of the recovered catalysts to impurities containing quinoline ring moieties. $^1$H NMR was measured with a GSX 270 type FT-NMR apparatus manufactured by Japan Electron Optics Datum Co., Ltd.

EXAMPLE 1

Molecular sieve 4A (10 mg) was added to a solution of N-allyloxycarbonyl-4-benzyl-1,3-oxazoline-2,5-dione (substrate (1)a; 27.5 mg, 0.1 mmol) in anhydrous ether (4 ml) (concentration: 25 mmol/l) derived from phenylalanine, which is a racemic α-amino acid. The mixture was cooled to −60° C., and Me-QD (13.5 mg, 0.4 equivalent) was added to the mixture. After stirring for five minutes, a 5% anhydrous ethanol/ether solution (50 μl; ethanol: 0.6 equivalent) was added thereto slowly with a syringe. The reaction mixture was stirred at this temperature for 30 hours, and then a 0.2 N aqueous hydrochloric acid solution (5 ml) was added to the reaction mixture to stop the reaction. The temperature was raised to room temperature, the aqueous and organic layers were separated, and the aqueous hydrochloric acid layer was extracted with diethyl ether (2×2 ml). The combined organic layer was dried over anhydrous sodium sulfate, and the extraction solvent was evaporated under reduced pressure. A 20% water/tetrahydrofuran solution (5 ml) was added to the residue, followed by stirring at room temperature overnight. The resulting solution was concentrated, the residue was dissolved in ether (3 ml), and the obtained solution was extracted with a 1 N aqueous sodium carbonate solution (2×3 ml). The organic layer was washed with water (1 ml) and dried over anhydrous sodium sulfate. After filtration, the filtrate was concentrated to give an optically active amino acid ester, namely, an R configuration ester (R-2a) (144 mg, yield: 52%). Enantiomer excess of the amino acid ester measured by HPLC analysis was 81% ee (s value=49).

The above-mentioned aqueous sodium carbonate layer was adjusted to pH 3 with a 2 N aqueous hydrochloric acid solution, and extracted with ethyl acetate (2×2 ml). The organic layer was dried over anhydrous sodium sulfate, and the extraction solvent was evaporated under reduced pressure to give an optically active substance of the above-mentioned α-amino acid, namely, an S configuration amino acid (S-3a) (90 mg, yield: 36%). Enantiomer excess of the amino acid measured by HPLC analysis was 99% ee.

The reactions in this Example are illustrated by the following formula (1).

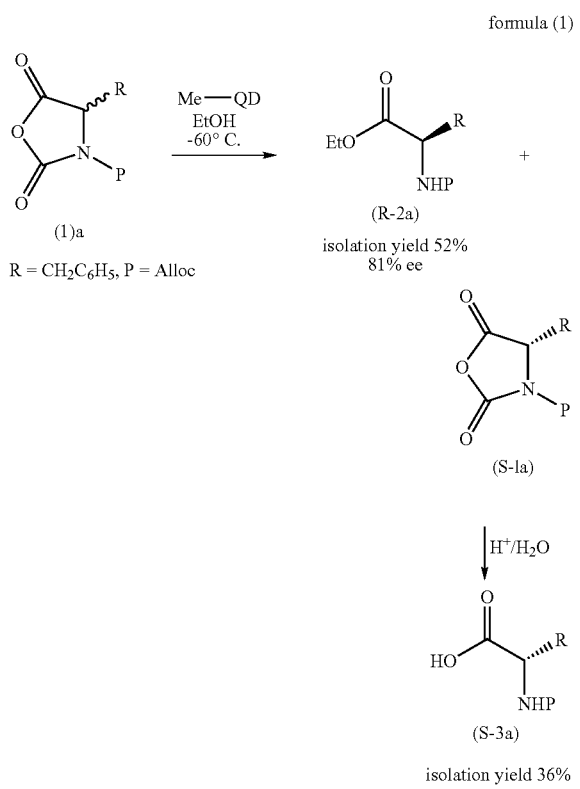

In Table 1, the substrates are the above-mentioned substrates (1)a, (1)b, (1)c and (1)d. In Table 2, the esters are S configuration esters (S-2a, S-2b, S-2c and S-2d) corresponding to the R configuration ester (R-2a) in Example 1, and the amino acids are R configuration amino acids (R-3a, R-3b, R-3c and R-3d) corresponding to the S configuration amino acid (S-3a) in Example 1.

EXAMPLE 34

An experiment was performed in the same manner as in Example 1 except that the reagents, the reaction conditions and the like were changed as shown in Table 1 to give results shown in Table 2.

The reaction in this Example is represented by the formula (2).

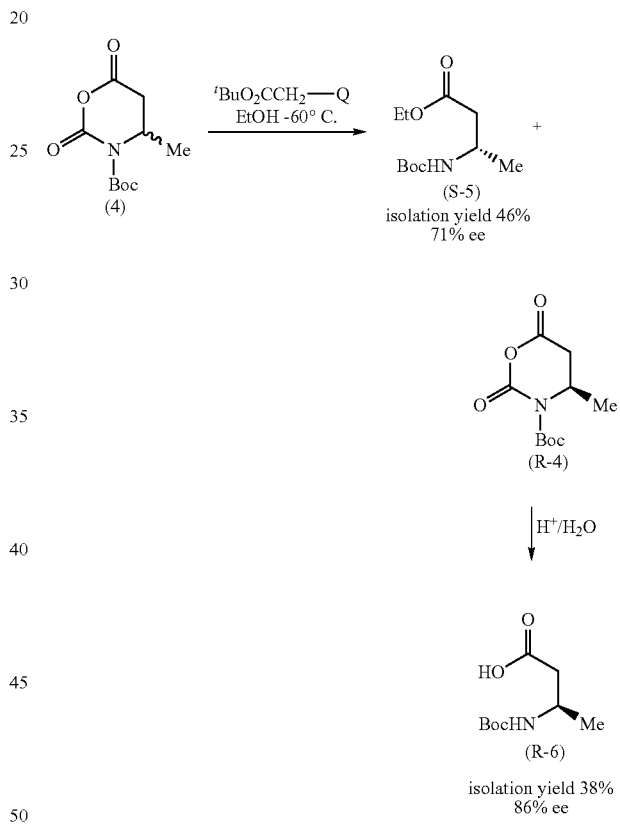

In order to recover the catalyst, the combined aqueous hydrochloric acid layer was adjusted to pH 10 with a 1 N aqueous sodium hydroxide solution, and extracted with ethyl acetate (2×2 ml). The organic layer was dried over anhydrous sodium sulfate, and the extraction solvent was evaporated under reduced pressure to give Me-QD (12.7 mg, recovery: 94%). Chemical purity of recovered Me-QD was 99% or higher according to $^1$H NMR analysis.

Tables 1 and 2 show the reagents, the reaction conditions, the reaction results and the like in Example 1.

COMPARATIVE EXAMPLE 1

An experiment was performed in the same manner as in Example 1 except that the catalyst, the reaction conditions and the like were changed as shown in Table 1 to give results shown in Table 2.

EXAMPLES 2 TO 33 AND COMPARATIVE EXAMPLES 2 TO 9

Experiments were performed in the same manner as in Example 1 except that the reagents, the reaction conditions and the like were changed as shown in Table 1 to give results shown in Table 2.

COMPARATIVE EXAMPLE 10

An experiment was performed in the same manner as in Example 34 except that the catalyst, the reaction conditions and the like were changed as shown in Table 1 to give results shown in Table 2.

EXAMPLE 35

An experiment was performed in the same manner as in Example 1 except that the reagents, the reaction conditions and the like were changed as shown in Table 1 to give results shown in Table 2.

The reaction in this Example is represented by the formula (3).

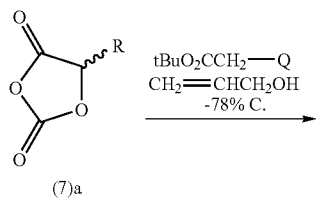

R = CH$_2$C$_6$H$_5$,

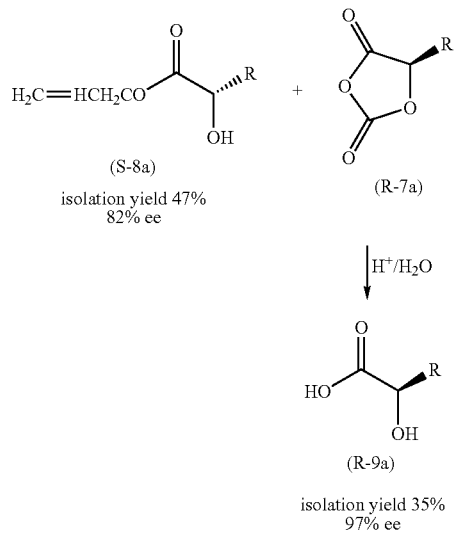

COMPARATIVE EXAMPLE 11

An experiment was performed in the same manner as in Example 35 except that the catalyst, the reaction conditions and the like were changed as shown in Table 1 to give results shown in Table 2.

EXAMPLE 36

An experiment was performed in the same manner as in Example 1 except that the reagents, the reaction conditions and the like were changed as shown in Table 1 to give results shown in Table 2 by dynamic kinetic optical resolution.

The reaction in this Example is represented by the formula (4).

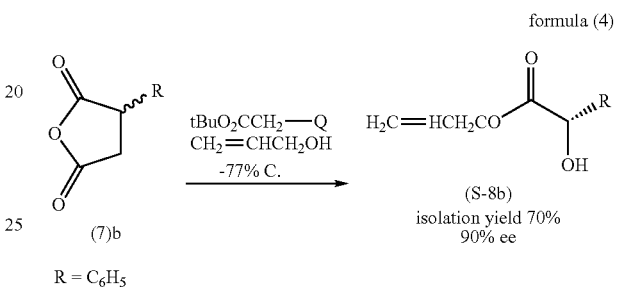

formula (4)

R = C$_6$H$_5$

EXAMPLE 37 AND COMPARATIVE EXAMPLE 12

Experiments were performed in the same manner as in Example 36 except that the catalyst, the reaction conditions and the like were changed as shown in Table 1 to give results shown in Table 2.

TABLE 1

| | Substrate | Solvent | Substrate Concentration [mmol/l] | Catalyst (equivalent) | Nucleophile (equivalent) | Reaction time [hr] | Reaction temperature [° C.] |
|---|---|---|---|---|---|---|---|
| Example 1 | (1)a | Et$_2$O | 25 | Me-QD(0.4) | EtOH(0.6) | 30 | −60 |
| Example 2 | (1)a | Et$_2$O | 25 | Me-Q(0.4) | EtOH(0.6) | 30 | −60 |
| Example 3 | (1)a | Et$_2$O | 25 | Bn-Q(04) | EtOH(0.6) | 34 | −60 |
| Example 4 | (1)a | Et$_2$O | 25 | CH$_2$=CHCH$_2$-Q(0.4) | EtOH(0.6) | 40 | −60 |
| Example 5 | (1)a | Et$_2$O | 25 | Et-Q(0.4) | EtOH(0.6) | 33 | −60 |
| Example 6 | (1)a | Et$_2$O | 25 | CH≡CCH$_2$-Q(0.4) | EtOH(0.6) | 30 | −60 |
| Example 7 | (1)a | Et$_2$O | 25 | $^t$BuO$_2$CCH$_2$-Q(0.4) | EtOH(0.6) | 33 | −60 |
| Example 8 | (1)a | Et$_2$O | 25 | MeOCH$_2$CH$_2$-Q(0.4) | EtOH(0.6) | 37 | −60 |
| Example 9 | (1)a | Toluene | 25 | Me-Q(0.4) | EtOH(0.6) | 20 | −60 |
| Example 10 | (1)a | Toluene | 125 | Me-Q(0.4) | EtOH(0.6) | 24 | −60 |
| Example 11 | (1)a | Et$_2$O | 125 | Me-Q(0.4) | EtOH(0.6) | 34 | −60 |
| Example 12 | (1)b | Et$_2$O | 25 | $^t$BuO$_2$CCH$_2$-Q(0.4) | MeOH(0.6) | 27 | −60 |
| Example 13 | (1)c | Et$_2$O | 25 | $^t$BuO$_2$CCH$_2$-Q(0.4) | CH$_2$=CHCH$_2$OH(0.6) | 25 | −78 |
| Example 14 | (1)d | Et$_2$O | 25 | $^t$BuO$_2$CCH$_2$-Q(0.4) | CF$_3$CH$_2$OH(0.6) | 41 | −60 |
| Example 15 | (1)a | Et$_2$O | 25 | HC≡CCH$_2$-HQ(0.4) | EtOH(0.6) | 35 | −60 |
| Example 16 | (1)a | Et$_2$O | 25 | HC≡CCH$_2$-CD(0.4) | EtOH(0.6) | 30 | −60 |
| Example 17 | (1)a | Et$_2$O | 25 | MeC≡CCH$_2$-Q(0.4) | EtOH(0.6) | 37 | −60 |
| Example 18 | (1)a | Et$_2$O | 25 | $^i$PrO$_2$CCH$_2$-Q(0.4) | EtOH(0.6) | 30 | −60 |
| Example 19 | (1)a | Et$_2$O | 25 | o-MeOC$_6$H$_4$CH$_2$-Q(0.4) | EtOH(0.6) | 27 | −60 |
| Example 20 | (1)a | Et$_2$O | 25 | o-ClC$_6$H$_4$CH$_2$-Q(0.4) | EtOH(0.6) | 30 | −60 |
| Example 21 | (1)a | Et$_2$O | 25 | 2-PyCH$_2$-Q(0.4) | EtOH(0.6) | 29 | −60 |
| Example 22 | (1)a | Et$_2$O | 25 | 2-FurCH$_2$-Q(0.4) | EtOH(0.6) | 37 | −60 |
| Example 23 | (1)a | Et$_2$O | 25 | 2-ThCH$_2$-Q(0.4) | EtOH(0.6) | 30 | −60 |
| Example 24 | (1)a | Et$_2$O | 25 | Me$_2$C=CHCH$_2$-Q(0.4) | EtOH(0.6) | 30 | −60 |
| Example 25 | (1)a | Et$_2$O | 25 | H$_2$NCOCH$_2$-Q(0.4) | EtOH(0.6) | 31 | −60 |
| Example 26 | (1)a | Et$_2$O | 25 | Et$_2$NCOCH$_2$-Q(0.4) | EtOH(0.6) | 27 | −60 |
| Example 27 | (1)a | Et$_2$O | 25 | NCCH$_2$-Q(0.4) | EtOH(0.6) | 33 | −60 |

TABLE 1-continued

| | Substrate | Solvent | Substrate Concentration [mmol/l] | Catalyst (equivalent) | Nucleophile (equivalent) | Reaction time [hr] | Reaction temperature [° C.] |
|---|---|---|---|---|---|---|---|
| Example 28 | (1)a | Et$_2$O | 25 | cyclo-C$_3$H$_5$CH$_2$-Q(0.4) | EtOH(0.6) | 33 | −60 |
| Example 29 | (1)a | Et$_2$O | 25 | PhC≡CCH$_2$-Q(0.4) | EtOH(0.6) | 30 | −60 |
| Example 30 | (1)a | Et$_2$O | 25 | MeCOCH$_2$-Q(0.4) | EtOH(0.6) | 28 | −60 |
| Example 31 | (1)a | Et$_2$O | 25 | o-Q-Xy-Q(0.2) | EtOH(0.6) | 30 | −60 |
| Example 32 | (1)a | Et$_2$O | 25 | Q-(CH$_2$)$_4$-Q(0.2) | EtOH(0.6) | 28 | −60 |
| Example 33 | (1)a | Toluene | 125 | HC≡CCH$_2$-QD(0.4) | EtOH(0.6) | 31 | −60 |
| Example 34 | 4 | Et$_2$O | 25 | $^t$BuO$_2$CCH$_2$-Q(0.4) | EtOH(0.6) | 30 | −60 |
| Example 35 | (7)a | Et$_2$O | 25 | $^t$BuO$_2$CCH$_2$-Q(0.2) | CH$_2$=CHCH$_2$OH(1.0) | 20 | −78 |
| Example 36 | (7)b | Et$_2$O | 25 | $^t$BuO$_2$CCH$_2$-Q(0.2) | CH$_2$=CHCH$_2$OH(1.2) | 23 | −78 |
| Example 37 | (7)b | Et$_2$O | 25 | Q-CH$_2$C≡CH$_2$-Q(0.2) | CH$_2$=CHCH$_2$OH(1.2) | 27 | −60 |
| Comparative Example 1 | (1)a | Et$_2$O | 25 | QD(0.4) | EtOH(0.6) | 28 | −60 |
| Comparative Example 2 | (1)a | Et$_2$O | 25 | Q(0.4) | EtOH(0.6) | 29 | −60 |
| Comparative Example 3 | (1)b | Et$_2$O | 25 | Q(0.4) | MeOH(0.6) | 35 | −60 |
| Comparative Example 4 | (1)c | Et$_2$O | 25 | Q(0.4) | CH$_2$=CHCH$_2$OH(0.6) | 30 | −78 |
| Comparative Example 5 | (1)d | Et$_2$O | 25 | Q(0.4) | CF$_3$CH$_2$OH(0.6) | 43 | −60 |
| Comparative Example 6 | (1)a | Et$_2$O | 25 | HQ(0.4) | EtOH(0.6) | 29 | −60 |
| Comparative Example 7 | (1)a | Et$_2$O | 25 | CD(0.4) | EtOH(0.6) | 36 | −60 |
| Comparative Example 8 | (1)a | Toluene | 125 | QD(0.4) | EtOH(0.6) | 29 | −60 |
| Comparative Example 9 | (1)a | Toluene | 125 | (DHQD)$_2$AQN(0.2) | EtOH(0.6) | 33 | −60 |
| Comparative Example 10 | 4 | Et$_2$O | 25 | Q(0.4) | EtOH(0.6) | 39 | −60 |
| Comparative Example 11 | (7)a | Et$_2$O | 25 | Q(0.2) | CH$_2$=CHCH$_2$OH(1.0) | 27 | −78 |
| Comparative Example 12 | (7)b | Et$_2$O | 25 | Q(0.2) | CH$_2$=CHCH$_2$OH(1.2) | 24 | −78 |

TABLE 2

| | Conversion (%) | Ester | | s value | Amino acid | | Catalyst Purity before use (%) | Recovery (%) | Purity after recovery (%) |
|---|---|---|---|---|---|---|---|---|---|
| | | | ee % (yield %) | | | ee % (yield %) | | | |
| Example 1 | 55 | R-2a | 81(52) | 49 | S-3a | 99(36) | >99 | 94 | >99 |
| Example 2 | 51 | S-2a | 87(46) | 45 | R-3a | 91(42) | >99 | 92 | >99 |
| Example 3 | 55 | S-2a | 78(49) | 30 | R-3a | 96(38) | >99 | 95 | >99 |
| Example 4 | 54 | S-2a | 83(47) | 46 | R-3a | 97(38) | >99 | 96 | >99 |
| Example 5 | 56 | S-2a | 77(47) | 34 | R-3a | 98(37) | >99 | 94 | >99 |
| Example 6 | 53 | S-2a | 85(47) | 48 | R-3a | 97(38) | >99 | 94 | >99 |
| Example 7 | 54 | S-2a | 84(46) | 56 | R-3a | 99(38) | >99 | 91 | >99 |
| Example 8 | 53 | S-2a | 82(46) | 33 | R-3a | 93(37) | >99 | 96 | >99 |
| Example 9 | 54 | S-2a | 81(49) | 35 | R-3a | 95(37) | >99 | 97 | >99 |
| Example 10 | 55 | S-2a | 76(48) | 24 | R-3a | 93(38) | >99 | 96 | >99 |
| Example 11 | 58 | S-2a | 65(47) | 14 | R-3a | 90(36) | >99 | 96 | >99 |
| Example 12 | 54 | S-2b | 84(48) | 56 | R-3b | 99(38) | >99 | 90 | >99 |
| Example 13 | 52 | S-2c | 88(46) | 59 | R-3c | 96(36) | >99 | 91 | >99 |
| Example 14 | 53 | S-2d | 86(46) | 55 | R-3d | 96(36) | >99 | 92 | >99 |
| Example 15 | 52 | S-2a | 86(48) | 45 | R-3a | 94(40) | >99 | 94 | >99 |
| Example 16 | 58 | S-2a | 70(50) | 22 | R-3a | 98(38) | >99 | 94 | >99 |
| Example 17 | 51 | S-2a | 86(45) | 40 | R-3a | 90(40) | >99 | 95 | >99 |
| Example 18 | 52 | S-2a | 86(47) | 45 | R-3a | 95(39) | >99 | 93 | >99 |
| Example 19 | 55 | S-2a | 79(47) | 34 | R-3a | 94(37) | >99 | 94 | >99 |
| Example 20 | 55 | S-2a | 78(47) | 30 | R-3a | 94(38) | >99 | 96 | >99 |
| Example 21 | 57 | S-2a | 74(48) | 30 | R-3a | 99(38) | >99 | 96 | >99 |
| Example 22 | 58 | S-2a | 72(51) | 34 | R-3a | 99(34) | >99 | 96 | >99 |
| Example 23 | 57 | S-2a | 75(49) | 39 | R-3a | 99(34) | >99 | 94 | >99 |

TABLE 2-continued

|  | Conversion (%) | Ester | ee % (yield %) | s value |  | Amino acid ee % (yield %) | Catalyst Purity before use (%) | Recovery (%) | Purity after recovery (%) |
|---|---|---|---|---|---|---|---|---|---|
| Example 24 | 57 | S-2a | 75(48) | 39 | R-3a | 99(33) | >99 | 95 | >99 |
| Example 25 | 56 | S-2a | 78(50) | 44 | R-3a | 99(36) | >99 | 96 | >99 |
| Example 26 | 56 | S-2a | 76(48) | 29 | R-3a | 98(35) | >99 | 92 | >99 |
| Example 27 | 53 | S-2a | 84(46) | 42 | R-3a | 96(40) | >99 | 91 | >99 |
| Example 28 | 57 | S-2a | 74(48) | 30 | R-3a | 98(36) | >99 | 95 | >99 |
| Example 29 | 53 | S-2a | 84(47) | 42 | R-3a | 95(44) | >99 | 94 | >99 |
| Example 30 | 52 | S-2a | 85(46) | 40 | R-3a | 92(38) | >99 | 92 | >99 |
| Example 31 | 57 | S-2a | 74(51) | 30 | R-3a | 99(35) | >99 | 94 | >99 |
| Example 32 | 58 | S-2a | 72(48) | 34 | R-3a | 98(35) | >99 | 98 | >99 |
| Example 33 | 55 | R-2a | 80(47) | 40 | S-3a | 99(38) | >99 | 96 | >99 |
| Example 34 | 54 | S-5 | 82(47) | 40 | R-6 | 97(38) | >99 | 90 | >99 |
| Example 35 | 52 | S-8a | 88(46) | 59 | R-9a | 97(35) | >99 | 92 | >99 |
| Example 36 | 100 | S-8b | 90(70) | — | — | — | >99 | 91 | >99 |
| Example 37 | 100 | S-8b | 95(70) | — | — | — | >99 | 95 | >99 |
| Comparative Example 1 | 57 | R-2a | 74(48) | 30 | S-3a | 98(38) | >99 | 98 | 95 |
| Comparative Example 2 | 56 | S-2a | 71(47) | 18 | R-3a | 91(36) | >99 | 98 | 96 |
| Comparative Example 3 | 58 | S-2b | 65(54) | 14 | R-3b | 91(32) | >99 | 97 | 93 |
| Comparative Example 4 | 59 | S-2c | 61(52) | 11 | R-3c | 89(33) | >99 | 95 | 93 |
| Comparative Example 5 | 58 | S-2d | 63(53) | 12 | R-3d | 88(31) | >99 | 97 | 95 |
| Comparative Example 6 | 56 | S-2a | 70(49) | 17 | R-3a | 90(33) | >99 | 95 | 91 |
| Comparative Example 7 | 42 | S-2a | 60(37) | 6 | R-3a | 43(42) | >99 | 96 | 91 |
| Comparative Example 8 | 57 | R-2a | 63(50) | 11 | S-3a | 85(32) | >99 | 97 | 93 |
| Comparative Example 9 | 57 | R-2a | 72(48) | 23 | S-3a | 97(34) | >99 | 95 | >99 |
| Comparative Example 10 | 60 | S-5 | 56(55) | 9 | R-6 | 84(32) | >99 | 94 | 97 |
| Comparative Example 11 | 58 | S-8a | 69(55) | 20 | R-9a | 96(33) | >99 | 96 | 94 |
| Comparative Example 12 | 100 | S-8b | 68(65) | — | — | — | >99 | 93 | 95 |

R and S mean an R configuration and an S configuration respectively.

As shown by the above-mentioned table, higher enantiomer selectivity (s values) was obtained in Examples 1 to 8 and 12 to 35 compared with Comparative Examples 1 to 7, 10 and 11. Examples 36 and 37 are examples wherein dynamic kinetic optical resolution was performed, and higher enantiomer selectivity (optical purity) was obtained compared with Comparative Example 12. Examples 9 and 10 are examples wherein toluene was used as the solvent, and the substrate concentration in the latter was five times higher than that in the former. Examples 2 and 11 are examples wherein ethyl ether was used as the solvent, and the substrate concentration in the latter was five times higher than that in the former. When the substrate concentration is increased, the s value generally is lowered. However, when aromatic solvents such as toluene were used, the lowering in s value was smaller than those in the case of other solvents. Example 33 is an example wherein the reaction was performed in the high substrate concentration using toluene as the solvent, and higher enantiomer selectivity (s value) was obtained compared with Comparative Examples 8 and 9.

Higher purity after recovering the catalysts were obtained in Examples compared with Comparative Examples.

INDUSTRIAL APPLICABILITY

Efficient kinetic optical resolution of recemic carboxylic acid derivatives can be performed, particularly, enantiomer selectivity (s values) is improved, and catalysts can be recovered in high purity by the present invention.

The invention claimed is:
1. An optically active compound represented by the following general formula (C) or (D),

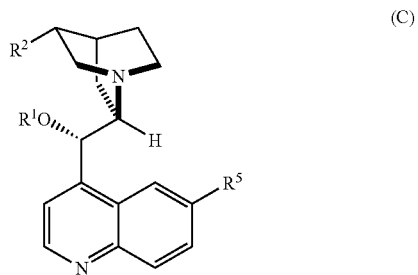

(C)

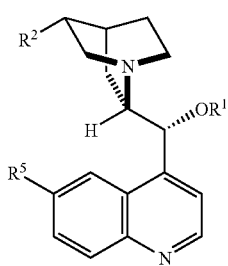
(D)

wherein R¹ is a group having one to 20 carbon atoms and represented by the following general formula (G), (H), or (J),

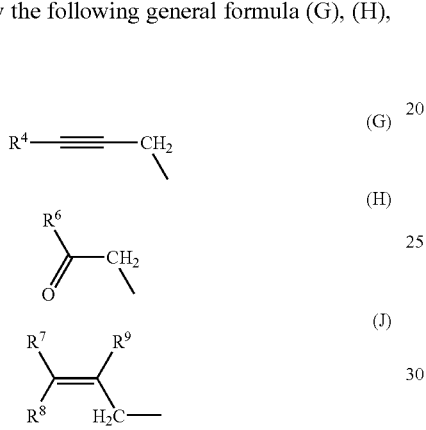
(G)

(H)

(J)

wherein $R^4$, $R^6$, $R^7$, $R^8$ and $R^9$, the same or different, are a hydrogen atom or a substituted or unsubstituted, saturated or unsaturated, straight-chain, branched or alicyclic aliphatic hydrocarbon group which can have an oxygen atom, or a substituted or unsubstituted aromatic hydrocarbon group, $R^2$ is ethyl or vinyl, and $R^5$ is a hydrogen atom or methoxy.

2. An optically active compound represented by the following general formula (C) or (D),

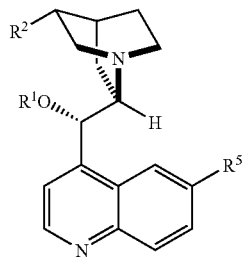
(C)

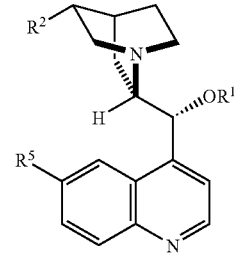
(D)

wherein R¹ is allyl, propynyl, tert-butoxycarbonylmethyl, 2-methoxyethyl, 2-butynyl, iso-propoxycarbonylmethyl, methoxycarbonylmethyl, o-methoxybenzyl, m-methoxybenzyl, p-methoxybenzyl, 2-pyridylmethyl, 3-pyridylmethyl, 4-pyridylmethyl, 2-furylmethyl, 3-furylmethyl, 2-thienylmethyl, 3-thienylmethyl, 1-naphthylmethyl, 2-naphthylmethyl, prenyl, cinnamyl, methallyl, homoallyl, homobenzyl, N,N-diethylaminocarbonylmethyl, cyanomethyl, acetylmethyl, cyclopropylmethyl, 3-phenyl-2-propynyl, 3-methoxycarbonyl-2-propynyl or 3-methoxycarbonyl-2-propenyl, $R^2$ is ethyl or vinyl, and $R^5$ is a hydrogen atom or methoxy.

3. An optically active compound according to claim 1, wherein $R^4$, $R^6$, $R^7$, $R^8$, and $R^9$, the same or different, are a hydrogen atom or a saturated or unsaturated hydrocarbon group which can have an oxygen atom, or an aromatic hydrocarbon group.

* * * * *